(12) United States Patent
Kudo

(10) Patent No.: US 6,802,833 B2
(45) Date of Patent: Oct. 12, 2004

(54) HYGIENE PRODUCT

(75) Inventor: Jun Kudo, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 14 days.

(21) Appl. No.: 10/351,565

(22) Filed: Jan. 24, 2003

(65) Prior Publication Data

US 2003/0149417 A1 Aug. 7, 2003

(30) Foreign Application Priority Data

Feb. 1, 2002 (JP) .................................. 2002-025924

(51) Int. Cl.[7] .................................................. A61F 13/15
(52) U.S. Cl. ........................ 604/385.02; 604/385.01; 604/385.04; 604/385.05; 206/440
(58) Field of Search .................... 604/385.02, 385.01, 604/385.04, 385.05; 206/440, 823

(56) References Cited

U.S. PATENT DOCUMENTS 6,074,376 A * 6/2000 Mills .......................... 604/390
6,575,947 B1 * 6/2003 Tameishi et al. ......... 604/385.01

FOREIGN PATENT DOCUMENTS

| JP | 6-75446 | 10/1994 | ........... A61F/13/15 |
| JP | 7-39820 | 7/1995 | ........... A61F/13/56 |
| JP | 09-285486 | 11/1997 | ........... A61F/13/15 |
| JP | 2000-005227 | 11/2000 | ........... A61F/13/15 |

* cited by examiner

Primary Examiner—John J. Calvert
Assistant Examiner—Jacqueline Stephens
(74) Attorney, Agent, or Firm—Darby & Darby

(57) ABSTRACT

Disclosed is a hygiene product including an absorbent article having a top layer for facing a wearer and a back layer having a pressure sensitive adhesive layer on a garment surface thereof, and a packaging sheet in which the absorbent article is wrapped. The packaging sheet has a first surface and a second surface. At least 50% of the top layer of the absorbent article faces the first surface of the packaging sheet. The pressure sensitive adhesive layer of the absorbent article is covered with a release sheet. The absorbent article is wrapped in the packaging sheet such that the second surface of the packaging sheet appears externally.

13 Claims, 17 Drawing Sheets

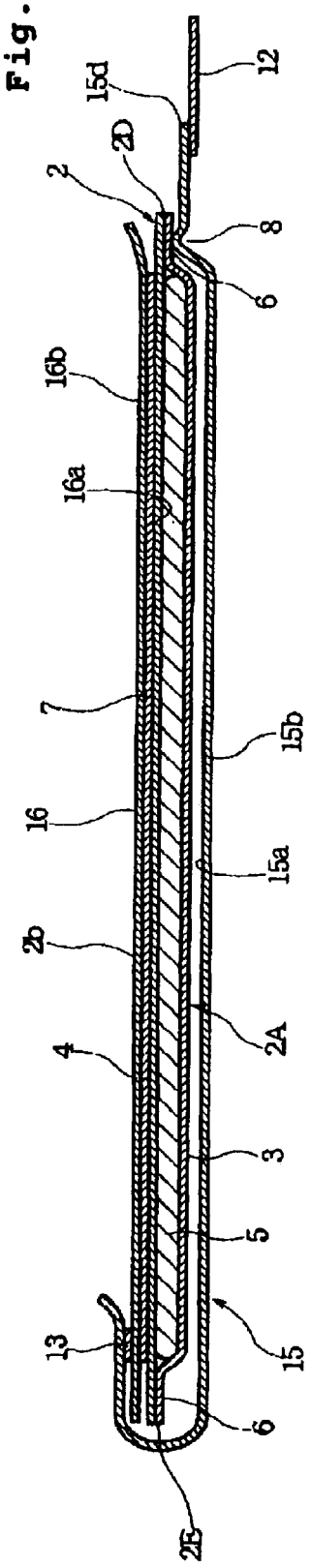

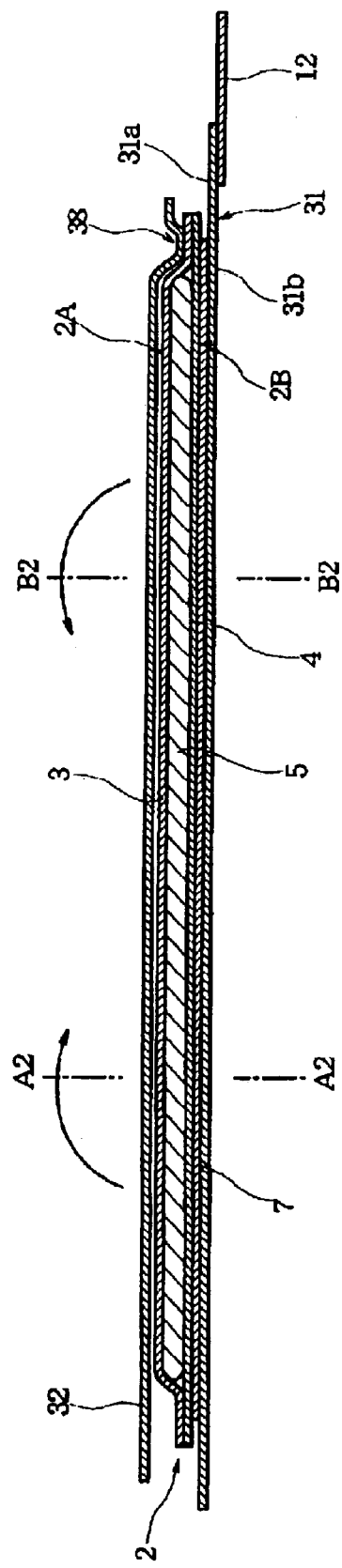

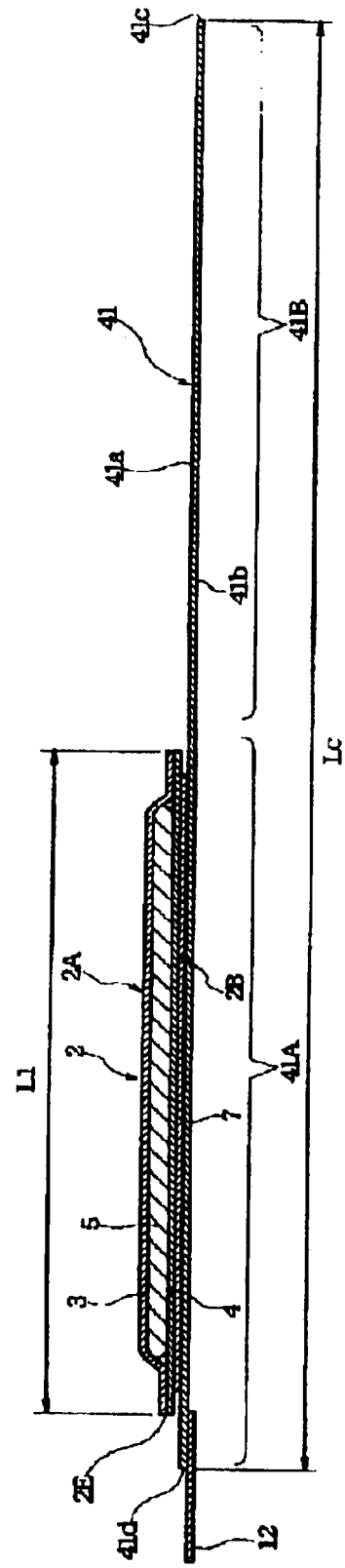
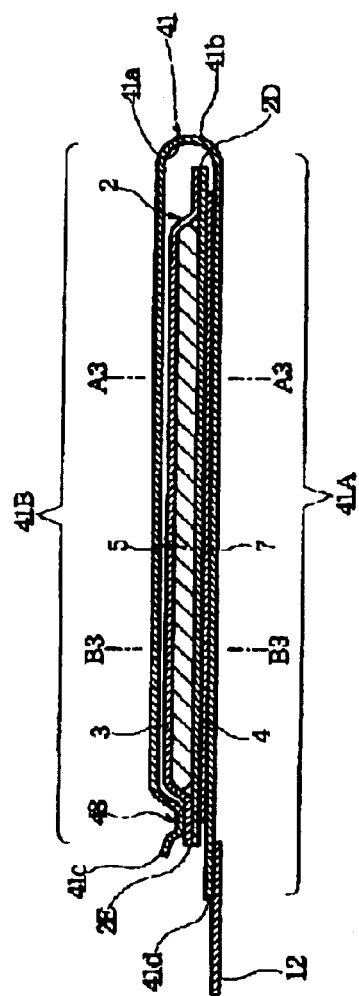
Fig. 12A
Fig. 12B

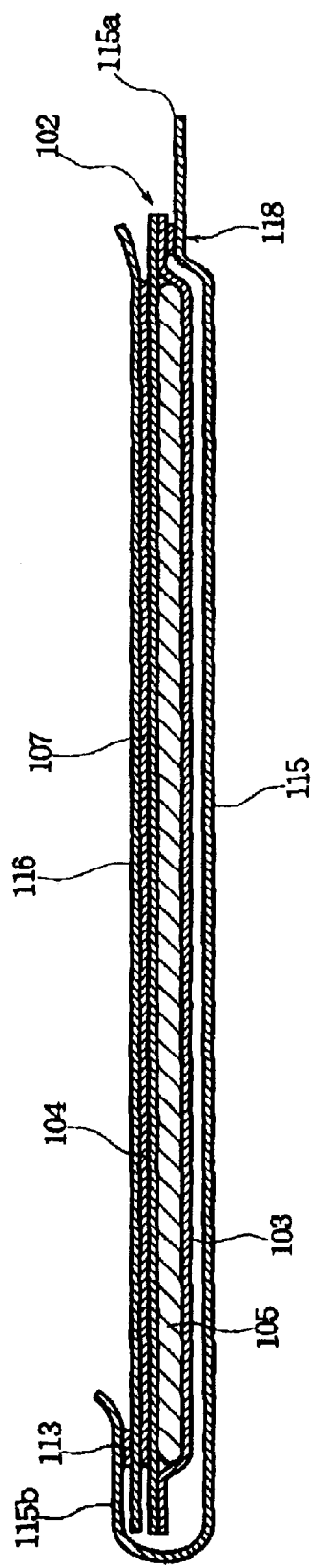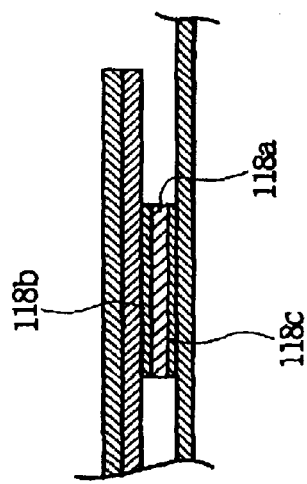
Fig. 17A
Fig. 17B

HYGIENE PRODUCT

BACKGROUND OF THE INVENTION

1. Field of the Invention

The present invention relates to a hygiene product wherein an absorbent article to be adhered to a crotch portion of an undergarment for wear, such as sanitary napkin, vaginal discharge absorbing sheet or incontinence pad, is individually wrapped in a packaging sheet.

2. Description of the Related Art

Absorbent articles such as sanitary napkin are constructed to include a liquid permeable top layer, a liquid impermeable back layer, and a liquid absorbent layer (absorbent core) disposed between the top layer and the back layer. On a garment surface of the back layer, there is usually provided a pressure sensitive adhesive layer so that the back layer can be adhered to a crotch portion of an undergarment through the pressure sensitive adhesive layer, thereby preventing displacement.

Such an absorbent article is individually wrapped in a packaging sheet. Japanese Unexamined Patent Publication No. 2000-5227 discloses such an individually packaged product, for instance.

In the individually packaged product disclosed in the above-identified publication, an adhesive layer provided on a garment surface of a backsheet of the absorbent article is protected by a release liner, and the release liner is adhered to the packaging sheet. The absorbent article, the release liner and the packaging sheet are folded together with a liquid permeable topsheet of the absorbent article being directed inward so that the packaging sheet appears externally.

When the absorbent article is taken out of the packaged product, the packaging sheet is peeled off as well as the adhesive layer of the backsheet is removed from the release liner. Then, the backsheet of the absorbent article is directed toward a crotch portion of an undergarment and the adhesive layer is adhered to the crotch portion of the undergarment.

On the other hand, Japanese Unexamined Utility-Model Publication Nos. 6-75446 (75446/1994) and 7-39820 (39820/1995) and Japanese Unexamined Patent Publication No. 9-285486 (285486/1997) disclose packaged products that are prepared by folding an absorbent article together with a packaging sheet, wherein an adhesive layer provided on a backsheet of the absorbent article is adhered to a release layer formed on the packaging sheet and both the backsheet and a topsheet of the absorbent article are covered with the packaging sheet.

In the packaged product disclosed in Japanese Unexamined Patent Publication No. 2000-5227, however, the topsheet of the absorbent article remains exposed externally until the adhesive layer is adhered to the crotch portion of the undergarment, after the packaging sheet is opened to remove the adhesive layer from the release liner. Therefore, the topsheet is liable to contact fingers during the opening operation. Here, it should be noted that the absorbent article is often pressed against the undergarment by laying a hand on the topsheet so as to certainly fix the adhesive layer to the crotch portion of the undergarment.

In the packaged products disclosed in Japanese Unexamined Utility-Model Publication Nos. 6-75446 (75446/1994) and 7-39820 (39820/1995) and Japanese Unexamined Patent Publication No. 9-285486 (285486/1997), on the other hand, although both the backsheet and the topsheet of the absorbent article are kept covered with the packaging sheet until use, since the release layer is formed on the packaging sheet, the packaging sheet will be completed separated from the absorbent article when the adhesive layer on the backsheet is peeled from the release layer. Accordingly, a wearer cannot help touching the topsheet when the adhesive layer on the backsheet is adhered to the crotch portion.

However, since the topsheet of the absorbent article comes into direct contact with the genital organ, it is usual for a wearer to wish to keep the topsheet clean, so that the wearer often hesitates about directly touching the topsheet with fingers. If the wearer washes her hands before attachment of the absorbent article to the undergarment, on the other hand, the topsheet can be kept clean but wet fingers may contact the topsheet. If the topsheet of the absorbent article is wetted with water that is adhering to the fingers, the wearer may feel that the topsheet is unsanitary.

Moreover, the use of water-disintegratable materials for a sanitary napkin or a vaginal discharge absorbing sheet is recently under consideration, but if wet fingers contact an absorbent article comprising water-disintegratable materials and water is given to the absorbent article, the strength of the topsheet and/or the backsheet may possibly decrease. In addition, if a garment attachment adhesive used for the water-disintegratable absorbent article is water-swellable one, the adhesive is swollen when applied water from fingers, so that adhesion between the absorbent article and the undergarment may decrease.

SUMMARY OF THE INVENTION

The present invention has been worked out in view of the shortcoming in the prior art set forth above. It is therefore an object of the present invention to provide a hygiene product in which an absorbent article can be adhered to a crotch portion of an undergarment without directly touching a top layer with fingers during removal of a packaging sheet.

According to a first aspect of the present invention, there is provided hygiene product comprising:

an absorbent article having a top layer for facing a wearer and a back layer having a pressure sensitive adhesive layer on a garment surface thereof; and a packaging sheet in which the absorbent article is wrapped, wherein the packaging sheet has a first surface and a second surface, at least 50% of the top layer of the absorbent article faces the first surface of the packaging sheet, and the pressure sensitive adhesive layer of the absorbent article is covered with a release sheet, wherein the absorbent article is wrapped in the packaging sheet such that the second surface of the packaging sheet appears externally.

In this hygiene product, since at least 50% of the top layer of the absorbent article can remain covered with the packaging sheet even after the packaging sheet is opened and the release sheet is peeled off, the absorbent article can be attached to an undergarment by pushing the top layer through the packaging sheet, so that fingers can be prevented from directly contacting the top layer.

Preferably, the packaging sheet is detachably fixed to the top layer of the absorbent article through temporal attachment means. If the packaging sheet is thus detachably fixed to the top layer, the top layer can be easily kept covered with the packaging sheet until the absorbent article is attached to the undergarment, thereby preventing fingers from directly contacting the top layer. Since the packaging sheet is detachably fixed to the top layer, moreover, the packaging sheet can be easily removed from the top layer after the absorbent article is attached to the undergarment.

Also preferably, the packaging sheet and the release sheet are connected to each other. In this case, the release sheet and the packaging sheet can be handled while being connected to each other even after removal of the release sheet from the adhesive layer, adhesion of the adhesive layer to the crotch portion of the undergarment and removal of the packaging sheet from the top layer, thereby facilitating the removal and disposal of the release sheet and the packaging sheet.

The absorbent article may have a main body portion and a pair of wing portions extending outwardly from longitudinally extending side edges of the main body portion. In this case, each wing portion may have a second pressure sensitive adhesive layer on a garment surface thereof and may be folded back against the release sheet so that the second pressure sensitive adhesive layer is adhered to the release sheet. With such construction, the second pressure sensitive adhesive layer can be protected by the release sheet.

According to a second aspect of the present invention, there is provided a hygiene product comprising:

an absorbent article having a top layer for facing a wearer and a back layer on a side opposite the top layer; and a packaging sheet in which the absorbent article is wrapped, wherein the absorbent article is wrapped in the packaging sheet with the packaging sheet being detachably fixed to the top layer of the absorbent article through temporal attachment means.

According to a third aspect of the present invention, there is provided a hygiene product comprising:

an absorbent article having a top layer for facing a wearer and a back layer having a pressure sensitive adhesive layer on a garment surface thereof; and a packaging sheet in which the absorbent article is wrapped, wherein the packaging sheet has a first surface and a second surface, the first surface has a release-treated portion, the pressure sensitive adhesive layer of the absorbent article is adhered to the release-treated portion of the packaging sheet, and at least 50% of the top layer is covered with a protective sheet, wherein the absorbent article is wrapped in the packaging sheet such that the second surface of the packaging sheet appears externally.

In this hygiene product, even after the packaging sheet is peeled from the absorbent article, at least 50% of the top layer of the absorbent article can remain covered with the protective sheet. Therefore, the absorbent article can be adhered to the crotch portion of the undergarment while protecting the top layer with the protective sheet.

Preferably, the protective sheet is detachably fixed to the top layer of the absorbent article through temporal attachment means. Also preferably, the packaging sheet and the protective sheet are connected to each other.

According to a fourth aspect of the present invention, there is provided a hygiene product comprising:

an absorbent article having a top layer for facing a wearer and a back layer on a side opposite the top layer; and a packaging sheet in which the absorbent article is wrapped, wherein the absorbent article is wrapped in the packaging sheet with a protective sheet being detachably fixed to the top layer of the absorbent article through temporal attachment means.

According to a fifth aspect of the present invention, there is provided a hygiene product comprising:

an absorbent article having a top layer for facing a wearer and a back layer on a side opposite the top layer; and a packaging sheet in which the absorbent article is wrapped, wherein the packaging sheet has a first surface and a second surface, the packaging sheet is folded such that the first surface faces both the top layer and the back layer of the absorbent article, and the packaging sheet is detachably fixed to the top layer of the absorbent article through temporal attachment means, wherein the absorbent article is wrapped in the packaging sheet such that the second surface of the packaging sheet appears externally.

Also in this case, since the packaging sheet is detachably fixed to the top layer of the absorbent article through temporal attachment means, the top layer can be kept covered with the packaging sheet until the absorbent article is attached to the undergarment.

If the back layer has a pressure sensitive adhesive layer on a garment surface thereof, the first surface of the packaging sheet may have a release-treated portion and the pressure sensitive adhesive layer may be adhered to the release-treated portion. Alternatively, a release sheet may be provided separately from the packaging sheet.

Here, individual side portions of the packaging sheet protruding transversely outwardly beyond transversely opposed side edges of the absorbent article may be sealed. In this case, the absorbent article can be wrapped in the packaging sheet without being folded together with the packaging sheet.

In the hygiene products according to the first to fifth aspects of the present invention, individual side portions of the packaging sheet protruding transversely outwardly beyond transversely opposed side edges of the absorbent article may be sealed after the packaging sheet is folded or rolled together with the absorbent article. Here, one end of the packaging sheet appearing externally may be detachably fixed to the second surface of the packaging sheet beneath the end. For instance, the fixation may be performed by using a tape having a pressure sensitive adhesive layer, a hot-melt type adhesive or heat seal.

With such seals, the absorbent article after folded or rolled hardly comes out of the packaging sheet. In addition, dust or the like hardly goes into the package. In the present invention, however, it is not necessarily required to seal the packaging sheet. Particularly when the pressure sensitive adhesive layer on the back layer of the absorbent article is adhered to the release-treated portion of the packaging sheet or the packaging sheet is fixed to the top layer of the absorbent article through the temporal attachment means, the absorbent article hardly comes out of the packaging sheet without the seals.

In the hygiene products, the absorbent article, the packaging sheet, the release sheet and the protective sheet may comprise water-disintegratable materials.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings:

FIG. 4 is a sectional view taken along line IV—IV of FIG. 2A;

FIG. 11 is a sectional view taken along line XI—XI of FIG. 9;

FIGS. 12A and 12B are sectional views showing how components are combined in a hygiene product according to a fourth embodiment of the present invention;

FIG. 17A is a sectional view showing a state where a hygiene product according to a seventh embodiment of the present invention is unfolded, and FIG. 17B is an enlarged view of a portion of FIG. 17A.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

As used herein, the hygiene product refers to an absorbent article individually wrapped in a packaging sheet. The absorbent article refers to an article having an ability to absorb a liquid, such as a sanitary napkin to be used by a woman during a menstrual cycle, a vaginal discharge absorbing sheet or panty liner to be used by a woman, and an incontinence pad to be used by a man or woman suffering from light urinary incontinence. It should be noted that the absorbent article and components thereof have a body surface and a garment surface. As used herein, the body surface means that surface of the article or components which is intended to be worn toward or adjacent to the body of a wearer, while the garment surface is on the opposite side and is intended to be worn toward or placed adjacent to an undergarment when the article is worn.

Figure 1:
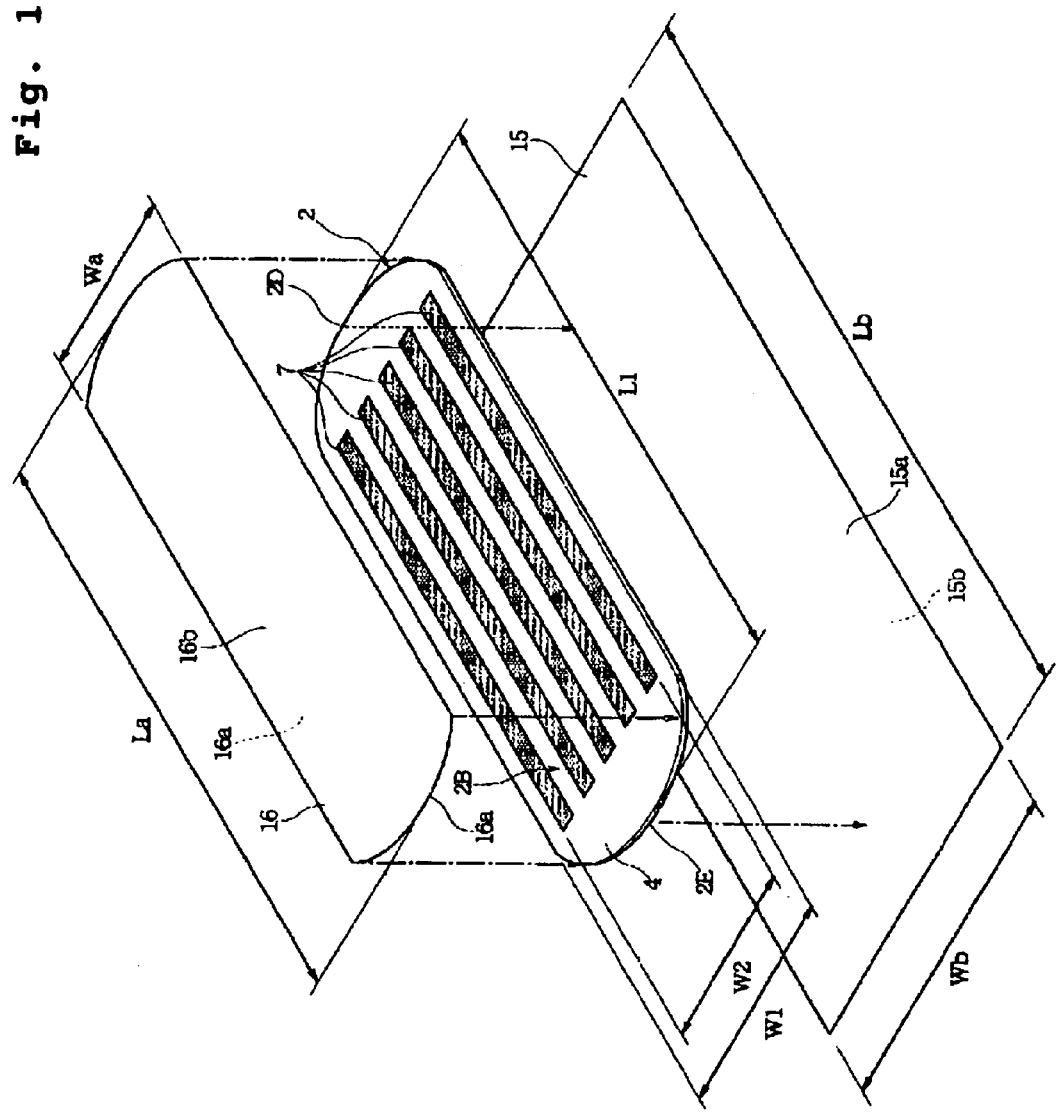
FIG. 1 is a perspective view showing an absorbent article, a release sheet and a packaging sheet forming a hygiene product according to a first embodiment of the present invention.
Figure 5:
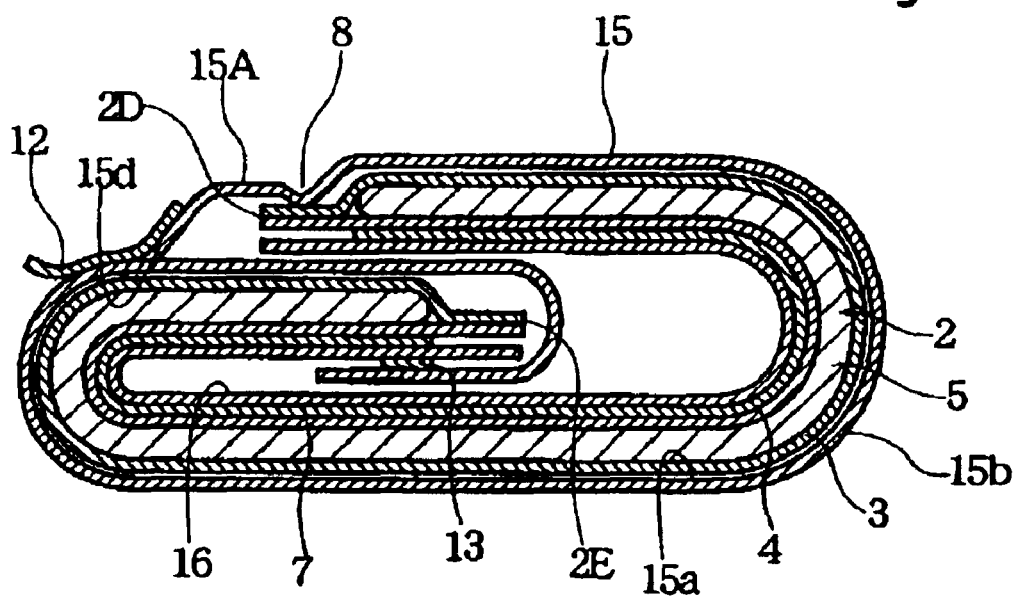
FIG. 5 is a sectional view taken along line V—V of FIG. 3A.

FIG. 1 is a perspective view showing components of a hygiene product 1 according to a first embodiment of the present invention; FIGS. 2A and 2B and FIGS. 3A and 3B are perspective views showing a folding procedure for forming the hygiene product 1; FIG. 4 is a sectional view taken along line IV—IV of FIG. 2A; and FIG. 5 is a sectional view taken along line V—V of FIG. 3A. It should be noted that the thickness is exaggerated in FIGS. 4 and 5.

The hygiene product 1 comprises an absorbent article 2, a packaging sheet 15 and a release sheet 16.

Figure 2A:
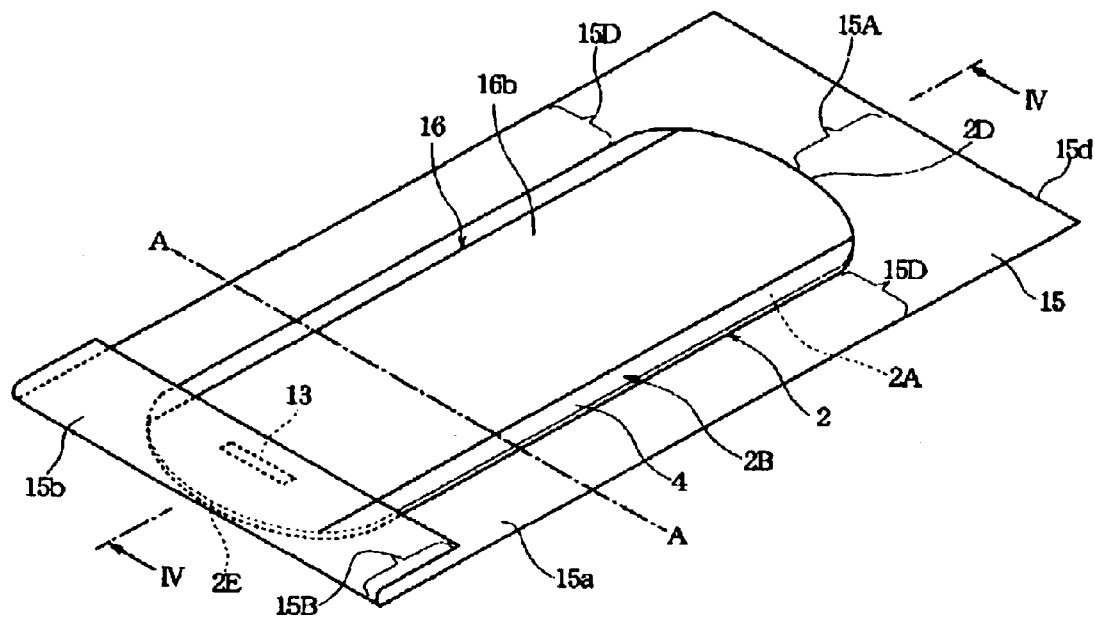
FIGS. 2A and 2B are perspective views showing a folding procedure for the first embodiment.

The absorbent article 2 has a body surface 2A for receiving a liquid and a garment surface 2B for facing a crotch portion of an undergarment. In FIGS. 1, 2A and 4, the body surface 2A is directed downward and the garment surface 2B is directed upward. As shown in FIG. 4, the absorbent article 2 comprises a top layer 3 appearing on the body surface 2A, a back layer 4 appearing on the garment surface 2B, and a liquid absorbent layer (absorbent core) 5 disposed between the top layer 3 and the back layer 4. The top layer 3 and the back layer 4 are of the same size, but the liquid absorbent layer 5 is slightly smaller than the top layer 3 and the back layer 4. In a region 6 outside the peripheral edge of the liquid absorbent layer 5, the top layer 3 and the back layer 4 are bonded to each other through a hot-melt type adhesive.

The top layer 3 of the absorbent article 2 is permeable to liquid and contains at least thermoplastic resin so as to be heat-fusible. In the embodiment shown, the top layer 3 is formed of a liquid permeable spunlaced nonwoven fabric comprising rayon fibers, polyester fibers and polypropylene fibers. In an alternative, the top layer 3 may be formed of a polyethylene film having a large number of liquid passage holes. The back layer 4 is impermeable to liquid and may be formed of a polyethylene sheet. The liquid absorbent layer 5 is a layer of fluff pulp or a layer of a mixture of fluff pulp and superabsorbent polymer. In an alternative, the liquid absorbent layer 5 may be of the thin type formed of air-laid pulp or a plurality of tissue paper.

In the case where the absorbent article 2 is of the type that is not required to absorb a large amount of liquid, such as panty liner, it is possible to absorb a liquid only with the top layer 3 without providing the liquid absorbent layer 5. In this case, the top layer 3 is a liquid absorbent sheet such as a nonwoven fabric comprising pulp, cotton and rayon fibers.

On the garment surface of the back layer 4 of the absorbent article 2, there is provided a pressure sensitive adhesive layer 7, as shown in FIGS. 1 and 4. The pressure sensitive adhesive layer 7 is formed by applying a pressure sensitive adhesive in an array of separate strips each having a predetermined width. These strips of the pressure sensitive adhesive layer 7 extend in a longitudinal direction of the absorbent article 2 and spaced apart from each other in a transverse direction of the absorbent article 2. The pressure sensitive adhesive layer 7 comprises a rubber adhesive or an acrylic adhesive.

The release sheet 16 has a first surface (release-treated surface) 16a that is directed toward the absorbent article 2 and a second surface 16b that is on the opposite side and is not treated with any release agent. A substrate of the release sheet 16 may be formed of a polyethylene sheet, a polypropylene sheet, paper or a laminate of paper and a resin sheet such as polyethylene or polyester. The first surface 16a may be formed by applying a release agent such as silicone resin or fluorine resin to one surface of the substrate.

The release sheet 16 may be of any shape and size as long as it can cover the entire pressure sensitive adhesive layer 7. In the first embodiment, the release sheet 16 has a width Wa larger than a width W2 of a region where the pressure sensitive adhesive layer 7 is provided in the absorbent article 2, but smaller than a width W1 of the absorbent article 2. On the other hand, the release sheet 16 has a length La substantially matching a length L1 of the absorbent article 2. It is, of course, possible that the release sheet 16 is larger than the absorbent article 2.

The packaging sheet 15 is a sheet that contains at least thermoplastic resin. In this embodiment, a polyethylene film is used. In an alternative, a nonwoven fabric containing at least one kind of fibers selected from polyethylene fibers, polyester fibers and polypropylene fibers may be used. The nonwoven fabric may be a spunbonded nonwoven fabric or spunbond-meltblown-spunbond (S-M-S) laminate.

In the first embodiment, the packaging sheet 15 is sufficiently larger than the absorbent article 2, and the packaging sheet 15 has a width Wb that is 1.05–1.3 times the width W1 of the absorbent article 2 and a length Lb that is 1.2–1.8 times the length L1 of the absorbent article 2.

The packaging sheet 15 has a first surface 15a that is directed toward the absorbent article 2 and a second surface 15b that is on the opposite side.

The absorbent article 2 is wrapped in the packaging sheet 15 as will be described hereinbelow.

At first, the pressure sensitive adhesive layer 7 appearing on the garment surface 2B of the absorbent article 2 is covered with the release sheet 16. At this time, adhered to the pressure sensitive adhesive layer 7 is the first, release-treated surface 16a of the release sheet 16.

Then, the absorbent article 2 is put on the first surface 15a of the packaging sheet 15 with the body surface 2A of the absorbent article 2 being directed toward the packaging sheet 15, as shown in FIG. 2A. Here, the packaging sheet 15 has a first protruding portion 15A protruding beyond one end edge 2D of the absorbent article 2 by a predetermined distance, a second protruding portion 15B protruding beyond the other end edge 2E of the absorbent article 2 by a predetermined distance, and side protruding portions 15D and 15D protruding beyond transversely opposed side edges of the absorbent article 2 by a predetermined distance. In addition, the packaging sheet 15 is detachably fixed at a portion indicated by 8 to the body surface 2A of the absorbent article 2, as shown in FIG. 4. At this fixed portion 8, the top layer 3 of the absorbent article 2 and the packaging sheet 15 are welded by sonic seal or heat seal. In an alternative, they may be engaged by needling. It is, of course, possible to bond them with a hot-melt type adhesive or a double-faced adhesive tape.

The fixed portion 8 is preferably adjacent to one end edge of the absorbent article 2. In this embodiment, the fixed portion 8 is adjacent to the end edge 2D of the absorbent article 2, while being spaced inwardly from the end edge 2D and outwardly from the liquid absorbent layer 5, as shown in FIG. 4.

In an alternative, the fixed portion 8 where the packaging sheet 15 is detachably fixed to the body surface 2A of the absorbent article 2 may be in a region where the liquid absorbent layer 5 is present. In this case, depending on the location and/or size of the fixed portion 8, liquid passage or liquid absorption may be blocked, as well as the condition of the top layer 3 may deteriorate to give a displeased feeling to a wearer or stimulate the wearer's skin or mucous membrane due to welding or bonding for formation of the fixed portion 8. In order to avoid such adverse effects, it is preferred that the fixed portion 8 is spaced away from the center of the top layer 3 as far as possible and made as small as possible.

It is also required that a force necessary to remove the packaging sheet 15 from the absorbent article 2 at the temporarily fixed portion 8 is larger than a force necessary to peel the release sheet 16 from the pressure sensitive adhesive layer 7. That is, it is required that when the release sheet 16 is peeled from the pressure sensitive adhesive layer 7 while holding the packaging sheet 15, the packaging sheet 15 is not separated at the fixed portion 8 from the absorbent article 2.

In order to prevent-breakage of the top layer 3 at the time when the packaging sheet 15 is removed from the absorbent article 2 as well as preventing undesirable separation of the packaging sheet 15 at the fixed portion 8 from the absorbent article 2, the fixed portion 8 is preferably formed by sonic seal to have a size of 5 mm×1 mm at three separate locations, for instance. In the case where a plurality of fixed portions 8 are provided, a peel strength is preferably in the range of 0.38 to 3.2 N, wherein the peel strength refers to a maximum force applied to the packaging sheet 15 when the packaging sheet 15 is cut into a piece having a width of 25 mm and peeled at 180° from the body surface 2A of the absorbent article 2 at a rate of 500 mm/min. Therefore, a peel strength between the release sheet 16 and the pressure sensitive adhesive layer 7 is preferably at most 0.33 N per 25 mm width.

If the area of the fixed portion 8 is too large, the top layer 3 may possibly be destroyed. Therefore, the fixed portion 8 occupies preferably at most 10%, more preferably at most 3% of the area of the absorbent article 2.

FIG. 2A shows a state where the second protruding portion 15B of the packaging sheet 15 is folded back so that the first surface 15a of the packaging sheet 15 at the second protruding portion 15B faces the second surface 16b of the release sheet 16, and the packaging sheet 15 and the release sheet 16 are firmly fixed to each other at a fixed portion 13. At the fixed portion 13, the packaging sheet 15 and the release sheet 16 are bonded through a hot-melt type adhesive or heat sealed so as not to easily separate from each other.

Conversely, it is also possible that one end of the release sheet 16 is extended beyond the end edge 2E of the absorbent article 2, folded back against the body surface 2A of the absorbent article 2, and partially fixed to the second surface 15b of the packaging sheet 15.

Figure 2B:
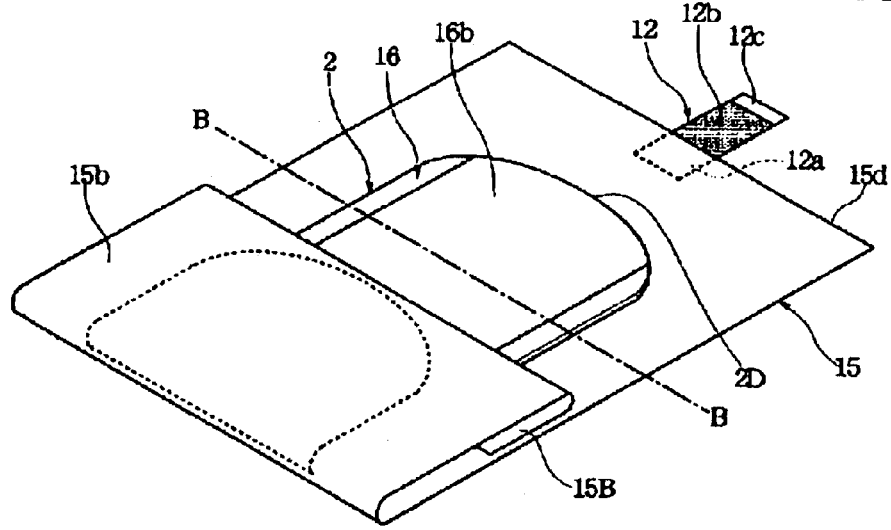

After formation of the fixed portions 8 and 13, the absorbent article 2, the release sheet 16 and the packaging sheet 15 are folded together as a unit about a first fold axis A—A transversely crossing the absorbent article 2. At this time, folding is performed such that the garment surface 2B of the absorbent article 2 faces inwardly and the second surface 15b of the packaging sheet 15 appears externally. FIG. 2B shows a state where the absorbent article 2, the release sheet 16 and the packaging sheet 15 are folded together about the first fold axis A—A.

Figure 3A:
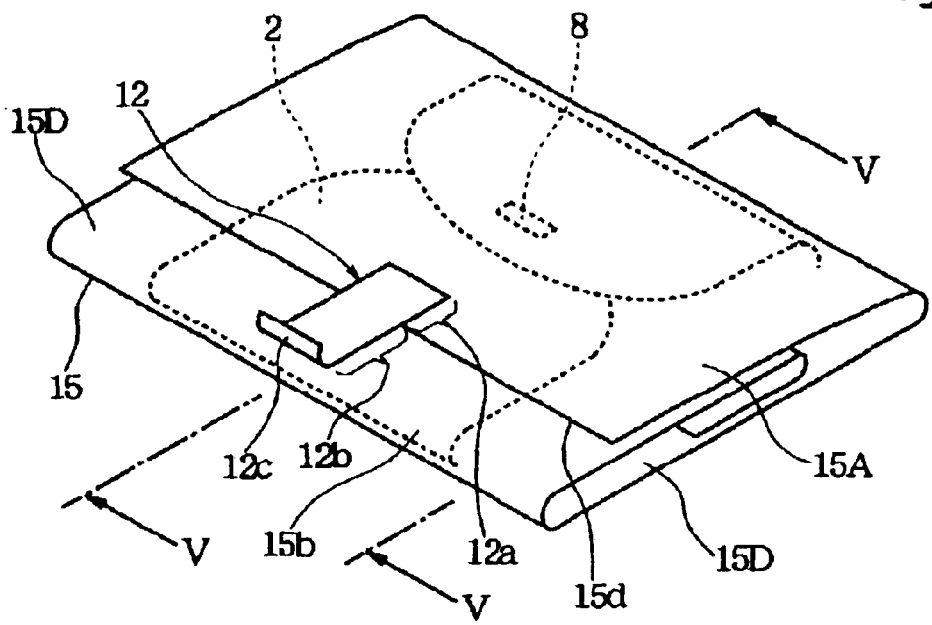
FIGS. 3A and 3B are perspective views showing a folding procedure for the first embodiment.

Then, the absorbent article 2, the release sheet 16 and the packaging sheet 15 are folded together about a second fold axis B—B of FIG. 2B. At this time, too, folding is performed such that the garment surface 2B of the absorbent article 2 faces inwardly and the second surface 15b of the packaging sheet 15 appears externally. As a result, the first protruding portion 15A of the packaging sheet 15 is laid on the second surface 15b of the previously folded back portion of the packaging sheet 15, so that the stack of the absorbent article 2, the release sheet 16 and the packaging sheet 15 is folded into three layers, as shown in FIGS. 3A and 5.

Here, as shown in FIG. 2B, the packaging sheet 15 is provided with a lead tape 12. This lead tape 12 is fixed to the second surface 15b of the packaging sheet 15 through an adhesive or by heat seal, thereby forming a fixed portion 12a. The lead tape 12 extends outwardly beyond an end edge 15d of the packaging sheet 15 to have a tab portion 12c having no pressure sensitive adhesive layer. Between the fixed portion 12a and the tab portion 12c, the lead tape 12 is provided with a pressure sensitive adhesive layer 12b. Therefore, when the stack is folded as shown in FIG. 3A, the portion of the lead tape 12 extending beyond the end edge 15d is adhered to the second surface 15b of the underlying portion of the packaging sheet 15 through the pressure sensitive adhesive layer 12b. It is, of course, possible to provide the pressure sensitive adhesive layer 12b over the entire length of the portion of the lead tape 12 extending outwardly beyond the end edge 15d, without providing the tap portion 12c. It is also possible to detachably fix a portion of the packaging sheet 15 adjacent to the end edge 15d to the second surface 15b of the underlying portion of the packaging sheet 15 through a hot-melt type adhesive or by heat seal, without providing the lead tape 12.

Figure 3B:
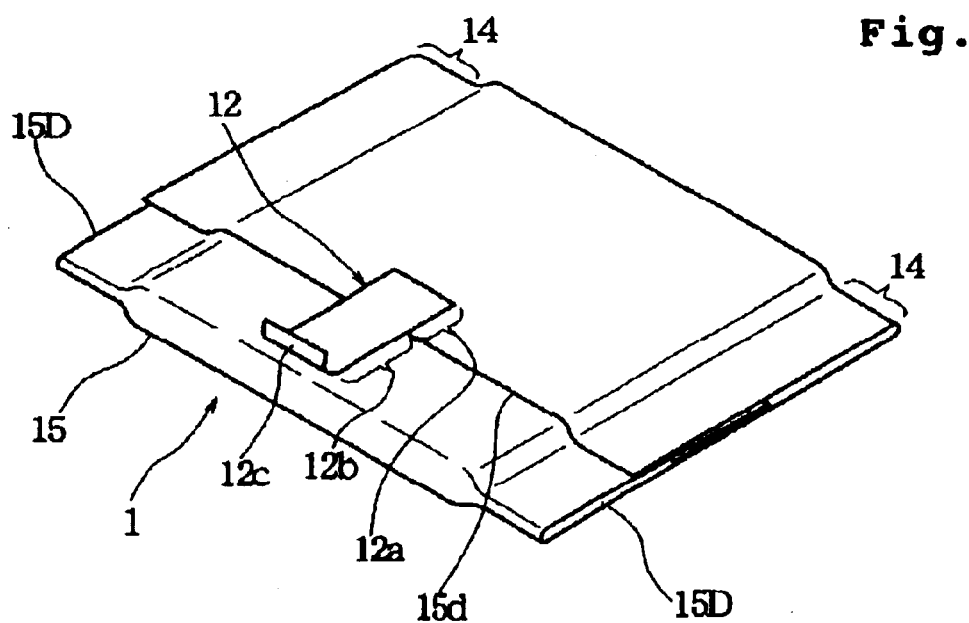

Moreover, as shown in FIG. 3B, the side protruding portions 15D and 15D of the packaging sheet 15 protruding beyond the side edges of the absorbent article 2 are bonded to themselves by heat seal or sonic seal, thereby forming side sealed portions 14 and 14, respectively. In an alternative, the packaging sheet 15 may be heat embossed to form the side sealed portions 14 and 14.

In the first embodiment, the hygiene product 1 is completed by forming the side sealed portions 14 and 14, as shown in FIG. 3B. However, the hygiene product may be completed in the state of FIG. 3A without forming the side sealed portions 14 and 14. That is, the folded state of the stack may be kept only with the lead tape 12.

Next, procedures for opening the hygiene product 1 of FIG. 3B and fixing the absorbent article 2 to an inner side of a crotch portion of an undergarment will be described.

At first, the portion of the lead tape 12 having the pressure sensitive adhesive layer 12b is peeled from the underlying portion of the packaging sheet 15, and then, the stack of the absorbent article 2, the release sheet 16 and the packaging sheet 15 is unfolded to the state of FIG. 2B, further to the state of FIG. 2A, while breaking the seal of the packaging sheet 15 at the side sealed portions 14 and 14. In the state of FIG. 2B or FIG. 2A, the release sheet 16 is peeled from the pressure sensitive adhesive layer 7 provided on the garment surface 2B of the absorbent article 2. The release sheet 16 thus peeled off still remains connected to the packaging sheet 15 at the fixed portion 13.

Then, the pressure sensitive adhesive layer 7 appearing on the garment surface 2B of the absorbent article 2 is adhered to an inner side of a crotch portion of an undergarment. During this operation, since the packaging sheet 15 is fixed at the fixed portion 8 to the body surface 2A of the absorbent article 2 and the top layer 3 of the absorbent article 2 is covered with the packaging sheet 15, the top layer 3 can be prevented from directly contacting fingers. In addition, since the absorbent article 2 can be pressed against the crotch portion through the packaging sheet 15 when the pressure sensitive adhesive layer 7 is adhered to the crotch portion of the undergarment, the absorbent article 2 can be certainly fixed to the crotch portion while preventing fingers or a hand from directly contacting the top layer 3 of the absorbent article 2.

After the absorbent article 2 is adhered to the crotch portion of the undergarment, the packaging sheet 15 is separated from the absorbent article 2 by peeling the packaging sheet 15 from the body surface 2A of the absorbent article 2 and breaking the fixation at the fixed portion 8. At this time, since the packaging sheet 15 and the release sheet 16 are connected to each other at the fixed portion 13, the packaging sheet 15 and the release sheet 16 can be disposed of in a connected state.

Here, it should be noted that the fixed portion 13 is not necessarily required, and the release sheet 16 and the packaging sheet 15 may not be connected to each other. In this case, only the release sheet 16 can be disposed of at the time when the release sheet 16 is peeled from the pressure sensitive adhesive layer 7. In this case, moreover, the end edge 2E of the absorbent article 2 may protrude outwardly from the packaging sheet 15 without providing the packaging sheet 15 with the second protruding portion 15B. That is, it is not necessarily required that the packaging sheet 15 covers the entire body surface 2A of the absorbent article 2. As long as at least 50% of the body surface 2A is covered, the body surface 2A can be protected when the absorbent article 2 is attached to the crotch portion of the undergarment. The covered area, is preferably at least 70%, more preferably 90%, of the body surface 2A. Most preferably, the entire body surface 2A is covered.

It should also be noted that although the fixed portion 8 is provided only near the end edge 2D of the absorbent article 2 in the first embodiment, a similar fixed portion where the packaging sheet 15 is detachably fixed to the body surface 2A of the absorbent article 2 may be optionally provided at a location different from the fixed portion 8. If such a fixed portion is provided near the end edge 2E of the absorbent article 2 in addition to the fixed portion 8 of FIG. 4 provided near the end edge 2D of the absorbent article 2, the body surface 2A of the absorbent article 2 can be certainly covered with the packaging sheet 15. The foregoing changes can also be adopted for the following embodiments.

Figure 6:
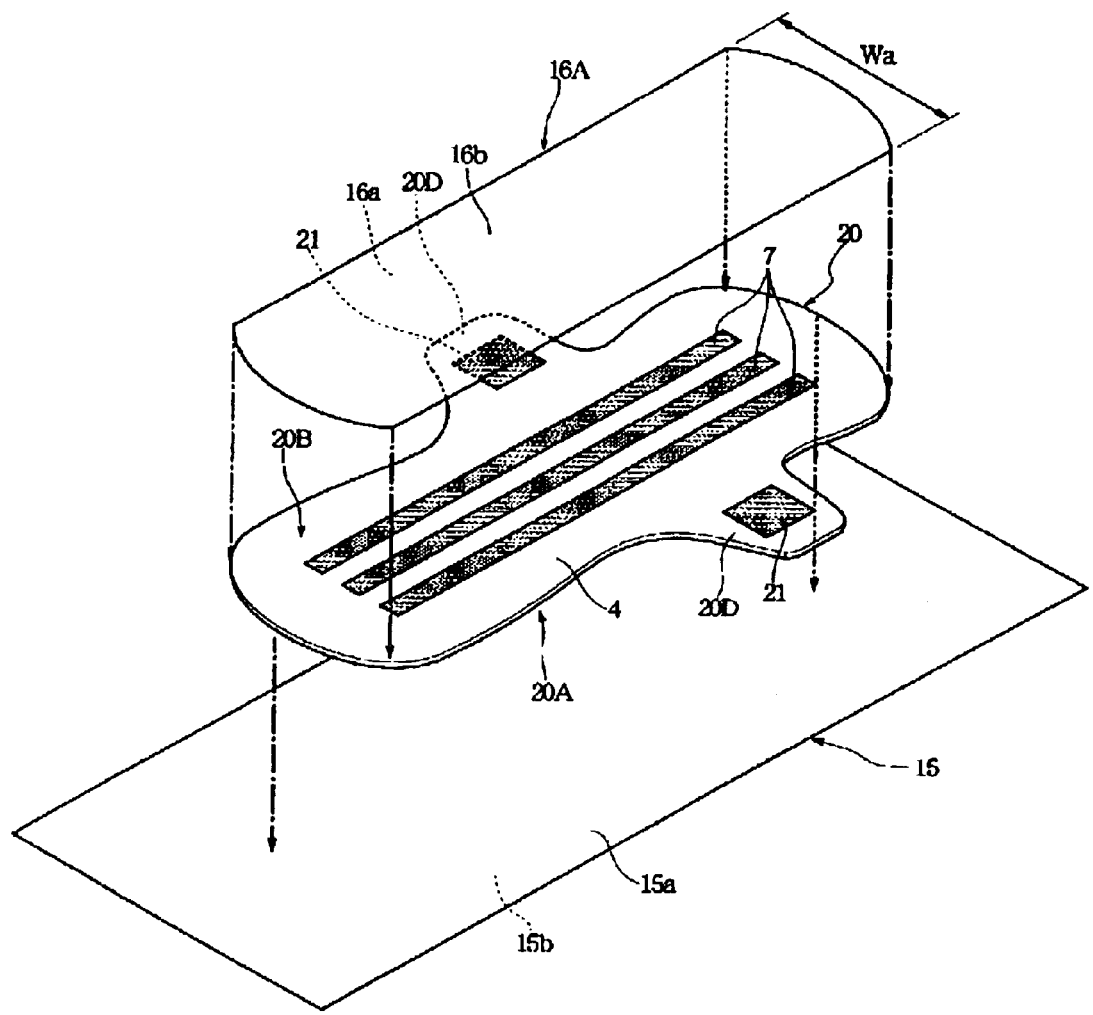
FIG. 6 is a perspective view showing an absorbent article, a release sheet and a packaging sheet forming a hygiene product according to a second embodiment of the present invention.
Figure 7A:
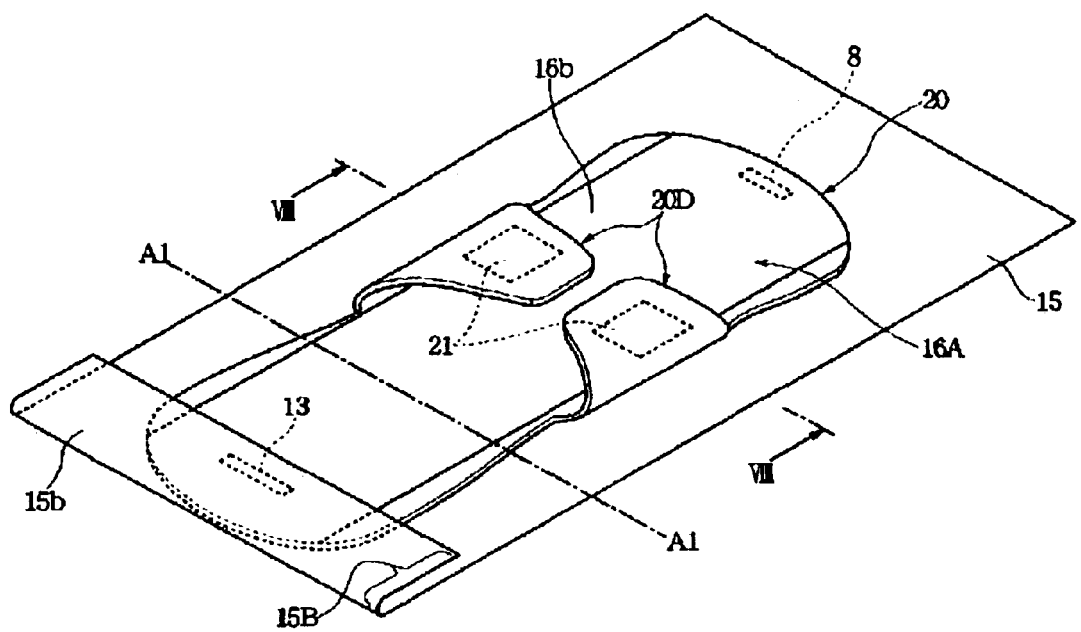
FIGS. 7A and 7B are perspective views showing a folding procedure for the second embodiment.
Figure 7B:
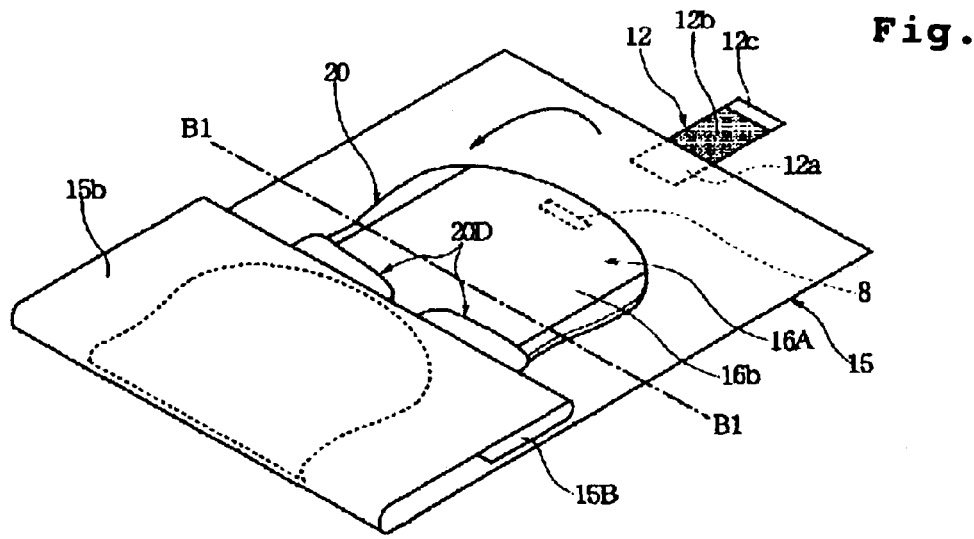
Figure 8:
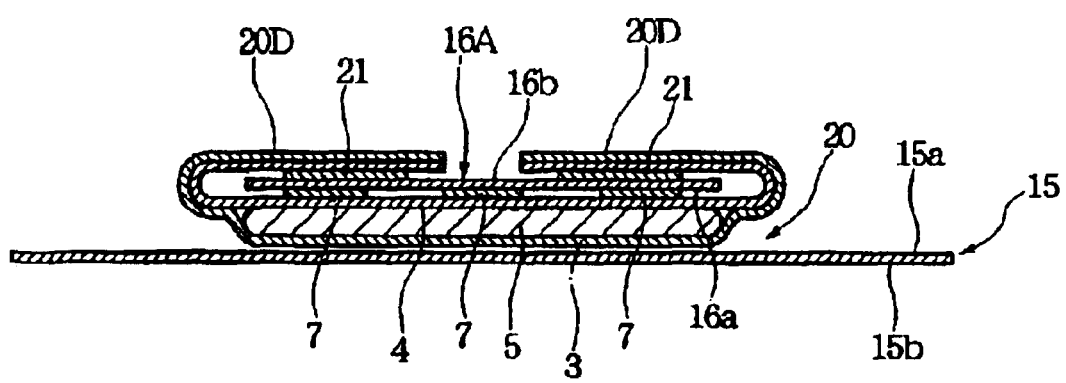
FIG. 8 is a sectional view taken along line VIII—VIII of FIG. 7A.

FIGS. 6 to 8 show a hygiene product according to a second embodiment of the present invention. The hygiene product of the second embodiment comprises an absorbent article 20, a release sheet 16A and the packaging sheet 15. FIG. 6 is a perspective view showing a state where the absorbent article 20, the release sheet 16A and the packaging sheet 15 are separated from each other; FIG. 7A is a perspective view showing a state where the absorbent article 20, the release sheet 16A and the packaging sheet 15 are stacked one on another and FIG. 7B is a perspective view showing a state where the stack is folded about a first fold axis; and FIG. 8 is a sectional view taken along line VIII—VIII of FIG. 7A. Hereinafter, the detailed description of the portions having the same constructions as those of the first embodiment will be omitted by designating them by the common reference numerals.

The absorbent article 20 has a main body portion that is comprised of the top layer 3, the back layer 4 and the liquid absorbent layer 5 as in the first embodiment, but the top layer 3 and the back layer 4 are further extended beyond the transversely opposed side edges of the main body portion to integrally form a pair of wing portions 20D and 20D. On the back layer 4 appearing on a garment surface 20B of the absorbent article 20, second pressure sensitive adhesive layers 21 and 21 are provided to be located within the wing portions 20D and 20D, in addition to the pressure sensitive adhesive layer 7 that is applied in an array of separate strips similar to those of FIG. 1.

The release sheet 16A has the first surface 16a that is directed toward the absorbent article 20 and the second surface 16b that is on the opposite side. In the second embodiment, however, both the first surface 16a and the second surface 16b are coated with a release agent such as silicone resin or fluorine resin, so that both the first surface 16a and the second surface 16b function as a release-treated surface.

Before the wing portions 20D and 20D are folded back, the pressure sensitive adhesive layer 7 is covered with the release sheet 16A, but the second pressure sensitive adhesive layers 21 and 21 remains uncovered with the release sheet 16A. In the second embodiment, the width Wa of the release sheet 16A is slightly smaller than the width of the main body portion of the absorbent article 20. As shown in FIGS. 7A and 8, after the first surface 16a of the release sheet 16A is adhered to the pressure sensitive adhesive layer 7, the wing portions 20D and 20D are folded back against the second surface 16b of the release sheet 16A so that the second pressure sensitive adhesive layers 21 and 21 provided on the wing portions 20D and 20D are adhered to the second surface 16b of the release sheet 16A.

Thereafter, the stack of the absorbent article 20, the release sheet 16A and the packaging sheet 15 is folded and sealed as in the first embodiment. That is, after the absorbent article 20 is laid on the packaging sheet 15 with its body surface 20A directed toward the first surface 15a of the packaging sheet 15, the packaging sheet 15 is detachably fixed at the fixed portion 8 to the body surface 20A of the absorbent article 20 and the release sheet 16A is firmly fixed at the fixed portion 13 to the packaging sheet 15. Then, the stack of the absorbent article 20, the release sheet 16A and the packaging sheet 15 is folded about a first fold axis A1—A1 and a second fold axis B1—B1 so that the second surface 15b of the packaging sheet 15 appears externally. In the second embodiment, the first fold axis A1—A1 and the second fold axis B1—B1 are provided so as not to cross the wing portions 20D and 20D, as shown in FIGS. 7A and 7B. After the stack of the absorbent article 20, the release sheet 16A and the packaging sheet 15 is folded to a state similar to that of FIG. 3A, the stack is sealed by the lead tape 12. Optionally, the side sealed portions 14 and 14 may be formed.

The hygiene product of the second embodiment can be used as follows. At first, after the stack of the absorbent article 20, the release sheet 16A and the packaging sheet 15 is unfolded to the state of FIG. 7A, the second pressure sensitive adhesive layers 21 and 21 provided on the wing portions 20D and 20D are peeled from the second surface 16b of the release sheet 16A, and then, the release sheet 16A is peeled from the pressure sensitive adhesive layer 7. Then, the main body portion of the absorbent article 20, of which the body surface 20A remains covered with the packaging sheet 15, is adhered to the crotch portion of the undergarment through the pressure sensitive adhesive layer 7, and then, the wing portions 20D and 20D are folded about side edges of the crotch portion of the undergarment and adhered to an outer side of the undergarment through the second pressure sensitive adhesive layers 21 and 21. Thereafter, the packaging sheet 15 is removed from the body surface 20A of the absorbent article 20.

Figure 9:
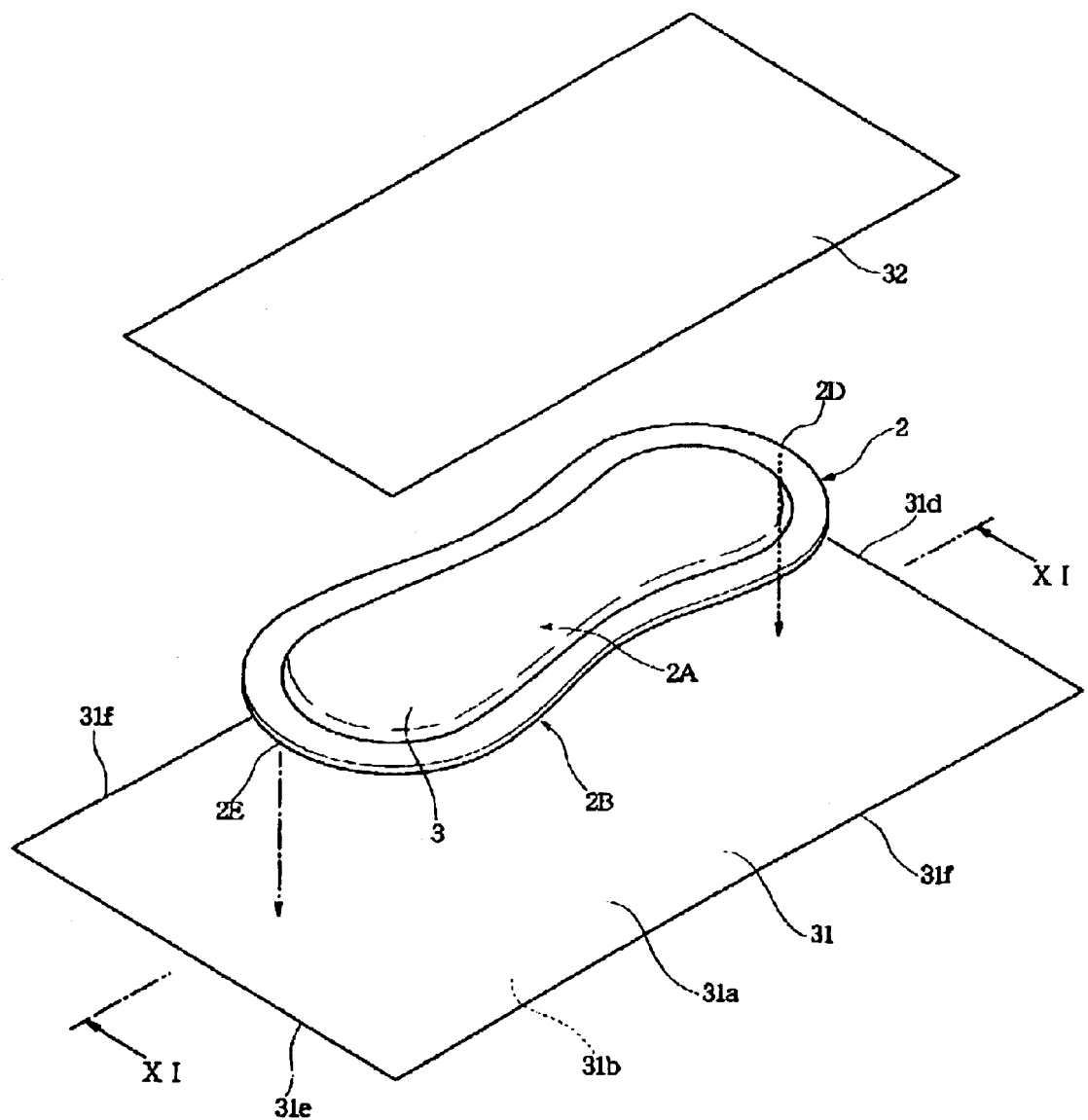
FIG. 9 is a perspective view showing an absorbent article, a protective sheet and a packaging sheet forming a hygiene product according to a third embodiment of the present invention.
Figure 10A:
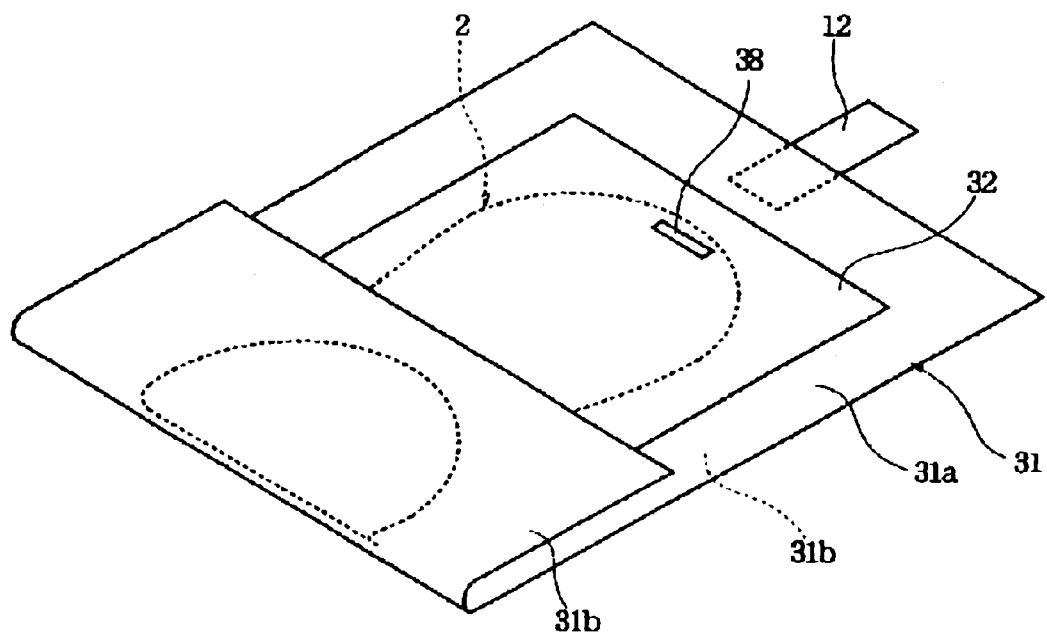
FIGS. 10A and 10B are perspective views showing a folding procedure for the third embodiment.
Figure 10B:
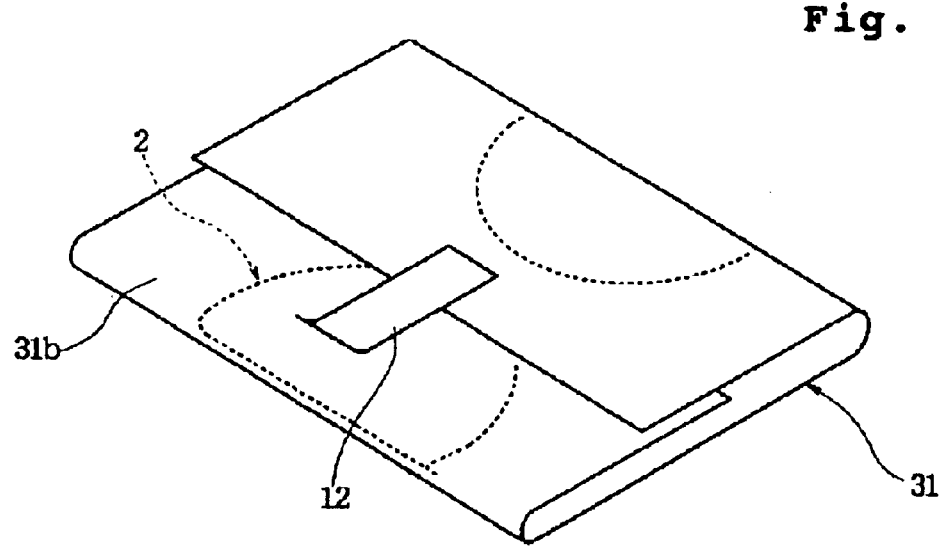

FIGS. 9 to 11 show a hygiene product according to a third embodiment of the present invention. The hygiene product of the third embodiment comprises the absorbent article 2, a packaging sheet 31 and a protective sheet 32. FIG. 9 is a perspective view showing a state where the absorbent article 2, the packaging sheet 31 and the protective sheet 32 are separated from each other; FIGS. 10A and 10B show a procedure for folding the stack of the absorbent article 2, the packaging sheet 31 and the protective sheet 32; and FIG. 11 is a sectional view taken along line XI—XI of FIG. 9.

In the third embodiment, as shown in FIG. 9, the absorbent article 2 is laid on the packaging sheet 31 with its garment surface 2B directed toward a first surface 31a of the packaging sheet 31. At least in a region for contacting the pressure sensitive adhesive layer 7, the first surface 31a of the packaging sheet 31 is provided with a release-treated portion. The release-treated portion can be formed variously as long as the pressure sensitive adhesive layer 7 can be easily peeled off. For example, the release-treated portion may be formed by applying a release agent such as silicone resin or fluorine resin to the first surface 31a of the packaging sheet 31, at least in a region for covering the pressure sensitive adhesive layer 7. In an alternative, a release sheet formed by applying a release agent such as silicone resin or fluorine resin to one surface of a substrate may be used with the other surface of the substrate fixed to the first surface 31a of the packaging sheet 31 through an adhesive. In the embodiment shown, the packaging sheet 31 is formed by applying a release agent to the first surface 31a of a substrate. For example, the substrate may be a spunbond-meltblown-spunbond laminate or paper, and the packaging sheet 31 may be formed by coating a polyethylene resin on the substrate and a silicone on the polyethylene resin. It is also possible to coat a silicone on a polyethylene sheet as a substrate.

In the third embodiment, the packaging sheet 31 is larger than the absorbent article 2. When the absorbent article 2 is laid thereon, as shown in FIG. 9, front and rear end edges 31d and 31e of the packaging sheet 31 are spaced outwardly from the front and rear end edges 2D and 2E of the absorbent article 2, respectively, as well as side edges 31f and 31f of the packaging sheet 31 are spaced outwardly from the side edges of the absorbent article 2. However, it is also possible that the end edge 2E of the absorbent article 2 is spaced outwardly from the end edge 31e of the packaging sheet 31, while the edges 31d, 31f and 31f are spaced outwardly from the corresponding edges of the absorbent article 2.

The protective sheet 32 is of a size that can cover at least 50% of the body surface 2A of the absorbent article 2. In the embodiment shown, however, the protective sheet 32 is larger than the body surface 2A of the absorbent article 2 so that the entire body surface 2A can be covered with the protective sheet 32. The protective sheet 32 is a heat-fusible sheet containing at least thermoplastic resin, such as a polyethylene sheet or a nonwoven fabric containing at least one kind of fibers selected from polyethylene fibers, polypropylene fibers and polyester fibers.

As shown in FIG. 11, the protective sheet 32 is detachably fixed at a fixed portion 38 to the body surface 2A of the absorbent article 2. The fixed portion 38 is formed by sonic seal or the like, similar to the fixed portion 8 of the first and second embodiments.

After the pressure sensitive adhesive layer 7 provided on the garment surface 2B of the absorbent article 2 is adhered to the release-treated portion of the first surface 31a of the packaging sheet 31 and the body surface 2A of the absorbent article 2 is covered with the protective sheet 32, the stack of the absorbent article 2, the protective sheet 32 and the packaging sheet 31 is folded about a first fold axis A2—A2 into a state of FIG. 10A. Then, it is folded about a second fold axis B2—B2 into a state of FIG. 10B so that a second surface 31b of the packaging sheet 31 appears externally. Thereafter, the packaging sheet 31 is secured by the lead tape 12. Optionally, the side sealed portions 14 and 14 may be formed, as shown in FIG. 3B.

The hygiene product of the third embodiment can be used as follows. At first, the stack of the absorbent article 2, the protective sheet 32 and the packaging sheet 31 is unfolded from the state of FIG. 10B by peeling the lead tape 12. Then, the packaging sheet 31 is peeled from the garment surface 2B of the absorbent article 2 to expose the pressure sensitive adhesive layer 7, and the garment surface 2B of the absorbent article 2 is adhered to the crotch portion of the undergarment through the pressure sensitive adhesive layer 7. During this operation, since the body surface 2A of the absorbent article 2 remains covered with the protective sheet 32, the top layer 3 of the absorbent article 2 can be prevented from undesirably contacting fingers. In addition, since the absorbent article 2 can be pressed against the crotch portion of the undergarment through the protective sheet 32, the absorbent article 2 can be certainly adhered to the crotch portion of the undergarment through the pressure sensitive adhesive layer 7 without touching the top layer 3. After the absorbent article 2 is adhered to the crotch portion, the protective sheet 32 is removed from the body surface 2A of the absorbent article 2 while breaking the fixation at the fixed portion 38.

It should be noted that although the protective sheet 32 and the packaging sheet 31 are not connected to each other in the third embodiment, the protective sheet 32 and the packaging sheet 31 may be connected to each other at a fixed portion similar to the fixed portion 13 of the first and second embodiments.

Figure 13A:
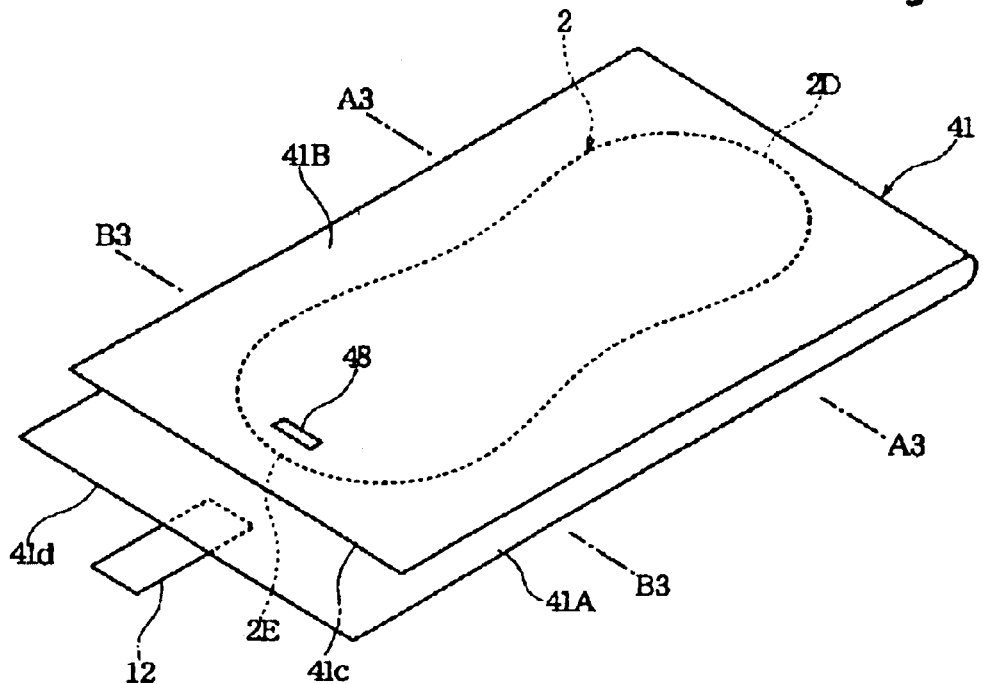
FIGS. 13A and 13B are perspective views showing a folding procedure for the fourth embodiment.
Figure 13B:
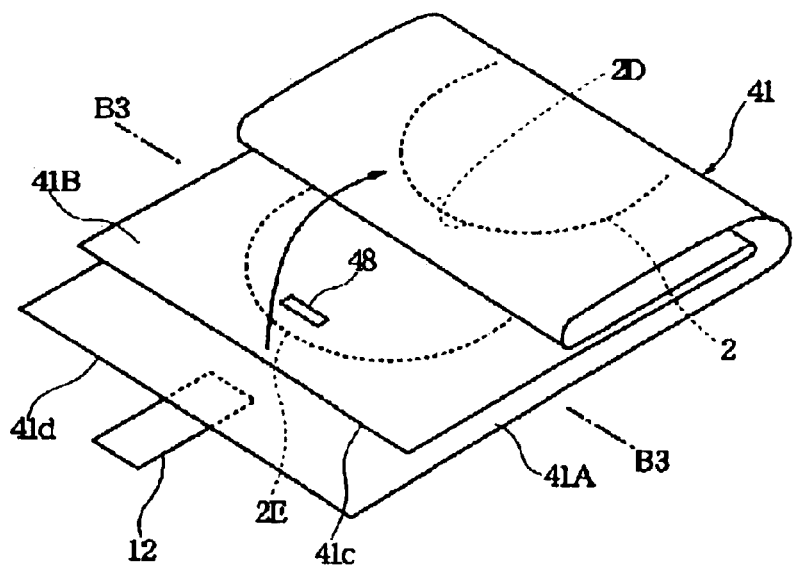

FIGS. 12A, 12B, 13A and 13B show a hygiene product according to a fourth embodiment of the present invention, wherein FIGS. 12A and 12B are sectional views showing a folding procedure and FIGS. 13A and 13B are perspective views showing a folding procedure as well.

The hygiene product of the fourth embodiment comprises the absorbent article 2 and a packaging sheet 41 that has a length Lc considerably larger than the length L1 of the absorbent article 2. In addition, the packaging sheet 41 has a width larger than the width W1 of the absorbent article 2.

The packaging sheet 41 has longitudinally opposed two regions: one being a release region 41A; the other being a protective region 41B.

The packaging sheet 41 has a first surface 41a and a second surface 41b that is on the opposite side. The packaging sheet 41 is formed of the same material as the packaging sheet 31 of the third embodiment, and at least in the release region 41A, the first surface 41a is provided with a release-treated portion.

After the pressure sensitive adhesive layer 7 provided on the garment surface 2B of the absorbent article 2 is adhered to the release-treated portion provided on the first surface 41a of the release region 41A, as shown in FIG. 12A, the protective region 41B extending outwardly beyond the end edge 2D of the absorbent article 2 is folded back against the body surface 2A of the absorbent article 2. As a result, the absorbent article 2 is sandwiched between the release region 41A and the protective portion 41B of the packaging sheet 41, as shown in FIGS. 12B and 13A.

In the embodiment shown, the length Lc of the packaging sheet 41 is at least twice the length L1 of the absorbent article 2, as shown in FIG. 12A, so that the release region 41A can cover the entire garment surface 2B of the absorbent article 2 and the protective region 41B can cover the entire body surface 2A of the absorbent article 2. However, the length Lc may be changed as long as the protective region 41B can cover at least 50% of the body surface 2A of the absorbent article 2.

As shown in FIGS. 12B and 13A, the protective region 41B of the packaging sheet 41 is detachably fixed to the body surface 2A of the absorbent article 2 at a location slightly spaced inwardly apart from an end edge 41c, thereby forming a fixed portion 48. The fixed portion 48 is similar in structure to the fixed portion 8 of FIG. 4 and the fixed portion 38 of FIG. 11. In the release region 41A, on the other hand, the lead tape 12 is fixed to the second surface 41b of the packaging sheet 41 through an adhesive. The lead tape 12 protrudes from an end edge 41d of the release region 41A.

The stack shown in FIGS. 12B and 13A is folded about a first fold axis A3—A3 into a state of FIG. 13B. At this time, folding is performed such that the second surface 41b of the release region 41A appears externally. Then, the stack is folded about a second fold axis B3—B3, so that the end edge 41d of the release region 41A is located on the outermost. Thereafter, packaging is finished by adhering the lead tape 12 protruding beyond the end edge 41d to the second surface 41b of the underlying portion of the packaging sheet 41, and optionally forming the side sealed portions 14 and 14, as shown in FIG. 3B.

The hygiene product of the fourth embodiment can be used as follows. At first, the stack of the absorbent article 2 and the packaging sheet 41 is unfolded to the state of FIGS. 12B and 13A by peeling the lead tape 12 from the packaging sheet 41. Then, the release region 41A of the packaging sheet 41 is peeled from the pressure sensitive adhesive layer 7 provided on the garment surface 2B of the absorbent article 2 to expose the pressure sensitive adhesive layer 7, and the garment surface 2B of the absorbent article 2 is adhered to the crotch portion of the undergarment through the pressure sensitive adhesive layer 7. During this operation, since the body surface 2A of the absorbent article 2 remains covered with the protective region 41B of the packaging sheet 41, the top layer 3 of the absorbent article 2 can be prevented from undesirably contacting fingers. In addition, since the absorbent article 2 can be pressed against the crotch portion of the undergarment through the protective region 41B, the absorbent article 2 can be certainly adhered to the crotch portion of the undergarment through the pressure sensitive adhesive layer 7 without touching the top layer 3. After the absorbent article 2 is adhered to the crotch portion, the packaging sheet 41 is removed from the body surface 2A of the absorbent article 2 while breaking the fixation at the fixed portion 48.

It should be noted that the stack of the absorbent article 2 and the packaging sheet 41 of the fourth embodiment may be folded about the first fold axis A3—A3 and the second fold axis B3—B3 in directions opposite to those of FIG. 13B. That is, the lead tape 12 may be attached to protrude from the end edge 41c of the protective region 41B and the stack may be folded about the first fold axis A3—A3 and the second fold axis B3—B3 so that the protective region 41B can appear externally.

Figure 14A:
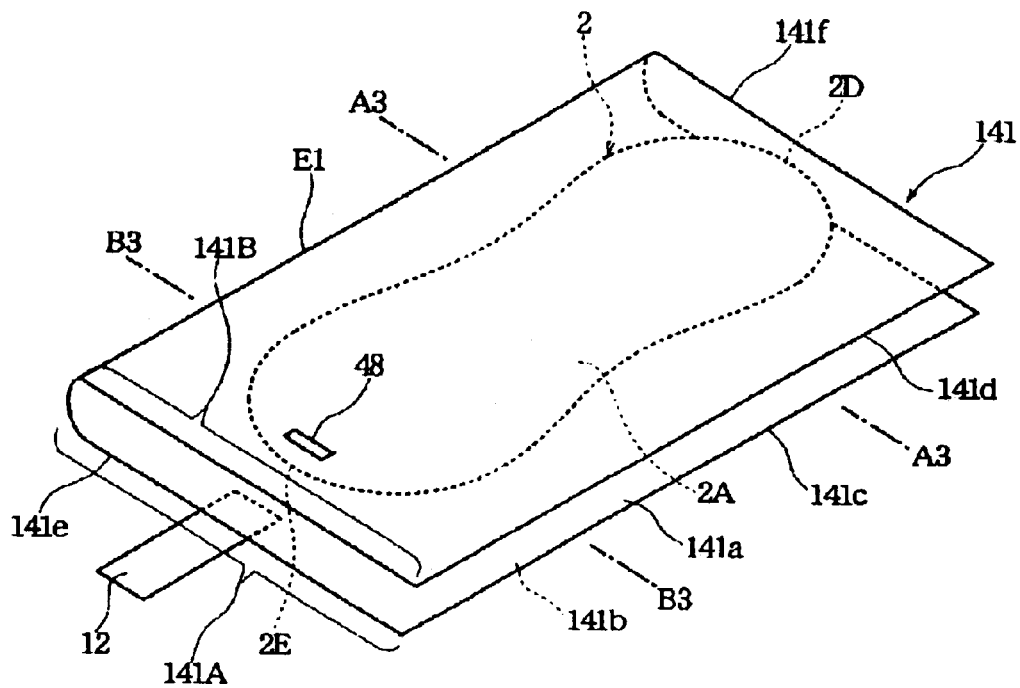
FIGS. 14A and 14B are perspective views showing a folding procedure for a fifth embodiment, which is a modification of the fourth embodiment.
Figure 14B:
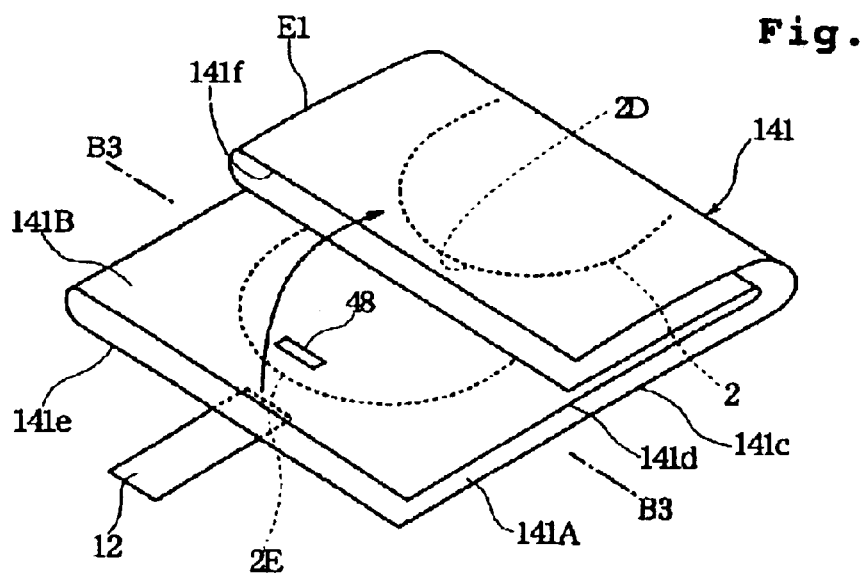

FIGS. 14A and 14B show a hygiene product according to a fifth embodiment of the present invention, which is a modification of the fourth embodiment. The hygiene product of the fifth embodiment comprises the absorbent article 2 and a packaging sheet 141.

The packaging sheet 141 has a first surface 141a and a second surface 141b. The packaging sheet 141 has a width that is at least twice the width W1 of the absorbent article 2. The packaging sheet 141 is divided along a fold line E1 into two regions: one being a release region 141A; the other being a protective region 141B. At least in the release region 141A, the first surface 141a is provided with a release-treated portion for covering the pressure sensitive adhesive layer 7 of the absorbent article 2.

As shown in FIG. 14A, after the pressure sensitive adhesive layer 7 provided on the garment surface 2B of the absorbent article 2 is adhered to the release-treated portion on the first surface 141a of the release region 141A, the packaging sheet 141 is folded such that edges 141c and 141d substantially coincide with each other, whereby the body surface 2A of the absorbent article 2 is covered with the protective region 141B. Then, the protective region 141B is detachably fixed at the fixed portion 48 to the body surface 2A of the absorbent article 2.

The stack thus formed is further folded as in the fourth embodiment. That is, the stack is folded firstly from the side of an edge 141f of the packaging sheet 141 and secondly from the side of an edge 141e, and secured by the lead tape 12 provided at the edge 141e. Optionally, the side sealed portions 14 and 14 may be formed along the fold line E1 and the edges 141c and 141d coinciding with each other.

Also in this embodiment, since the body surface 2A of the absorbent article 2 remains covered with the protective region 141B even after the release region 141A is peeled from the pressure sensitive adhesive layer 7 of the absorbent article 2, the absorbent article 2 can be attached to the crotch portion of the undergarment while preventing the top layer 3 from being soiled.

Here, it should be noted that although the edges 141c and 141d of the packaging sheet 141 substantially coincide with each other in FIGS. 14A and 14B, the release region 141A may be extended farther so that the edge 141c is spaced outwardly apart from the edge 141d and the extended portion of the release region 141A may be laid on the protective region 141B by further folding before folding about the fold axes A3—A3 and B3—B3.

Figure 15A:
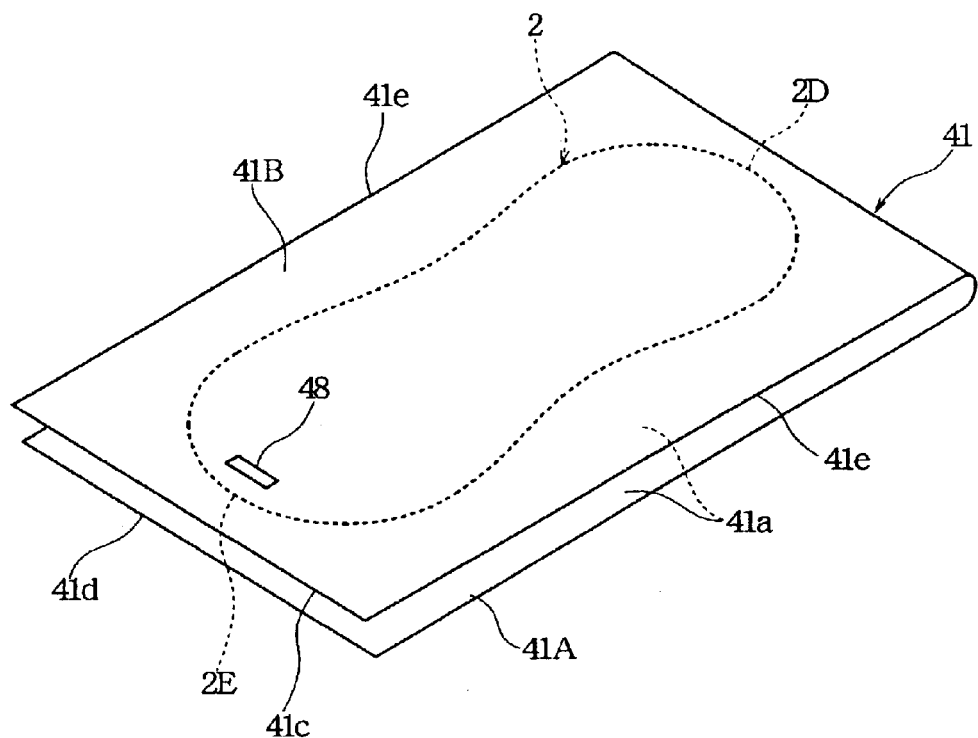
FIGS. 15A and 15B are perspective views showing how components are combined in a hygiene product according to a sixth embodiment of the present invention.
Figure 15B:
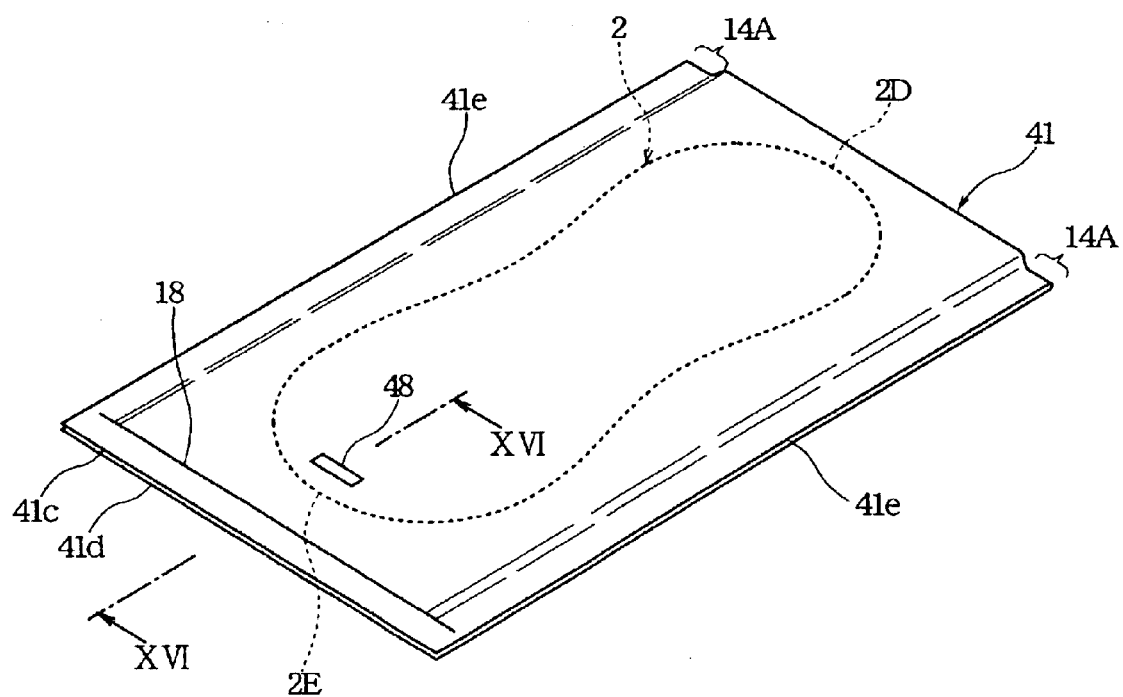
Figure 16A:
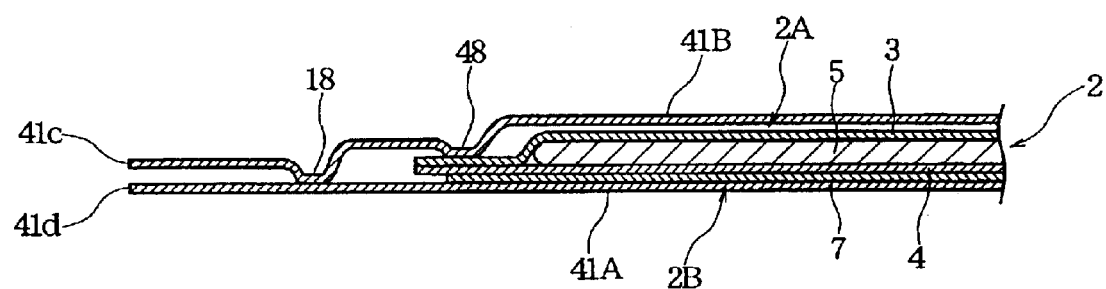
FIG. 16A is an enlarged sectional view taken along line XVI—XVI of FIG. 15B.
Figure 16B:
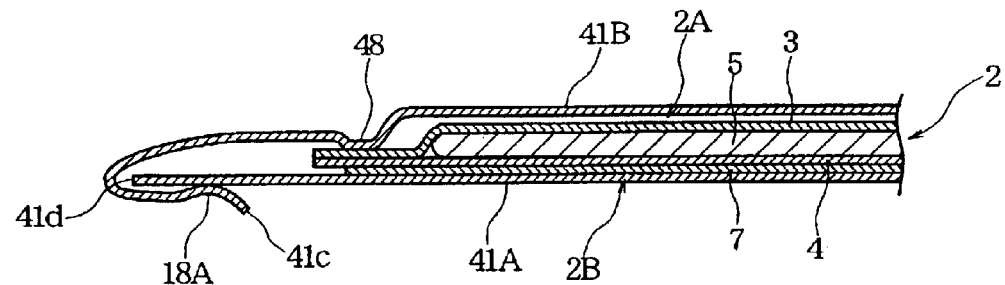
FIG. 16B is an enlarged sectional view showing a modification of the sixth embodiment.

FIGS. 15A and 15B are perspective views showing a hygiene product according to a sixth embodiment of the present invention; and FIG. 16A is an enlarged sectional view taken along line XVI—XVI of FIG. 15B, and FIG. 16B is an enlarged sectional view showing a modification of the sixth embodiment.

The packaging sheet 41 used in the embodiment of FIGS. 13A and 13B is also used in the sixth embodiment. As shown in FIG. 15A, the packaging sheet 41 is folded and longitudinally divided into two regions, wherein the pressure sensitive adhesive layer 7 on the garment surface 2B of the absorbent article 2 is adhered to the release region 41A and the body surface 2A of the absorbent article 2 is covered with the protective region 41B. The body surface 2A and the protective region 41B are detachably fixed to each other at a fixed portion 48.

In the state of FIG. 15A where the packaging sheet 41 is folded with the first surface 41a being directed inward, individual side edges 41e of the packaging sheet 41 are folded back on themselves outside the side edges of the absorbent article 2. Then, the packaging sheet 41 is bonded to itself by heat seal or sonic seal to form side sealed portions 14A that extend along the entire length of the side edges 41e and have a predetermined width inwardly of the side edges 41e, as shown in FIG. 15B.

The packaging sheet 41 is also sealed to itself at a location inwardly spaced apart from the end edges 41c and 41d to form a sealed portion 18 that extends linearly transversely of the packaging sheet 41.

Thus, the resulting hygiene product is made airtight with the side sealed portions 14A and the sealed portion 18 while the absorbent article 2 remains unfolded as shown in FIG. 15B. If the absorbent article 2 is small, it can be carried in such a flat state without folding. It is also possible to further fold the hygiene product from the state of FIG. 15B for carrying convenience.

When this hygiene product is to be used, the end edges 41c and 41d of the packaging sheet 41 are pulled and separated from each other, thereby breaking the seal at the sealed portion 18 and subsequently breaking the seal at the side sealed portions 14A and removing the release region 41A from the pressure sensitive adhesive layer 7. Thus, the absorbent article 2 can be attached to the crotch portion of the undergarment while keeping the body surface 2A covered with the protective region 41B.

FIG. 16B shows a modification of the sixth embodiment, wherein a sealed portion 18A is formed after a leading end of the protective region 41B is folded around the end edge 41d so that the end edge 41c is laid on the exterior surface of the release region 41A. Conversely, such a sealed portion may be formed after the end edge 41d is laid on the exterior surface of the protective region 41B. Alternatively, the lead tape 12 may be provided to extend from the end edge 41c and this lead tape 12 may be adhered to the exterior surface of the release region 41A, without forming the sealed portion 18 or 18A.

Likewise, the packaging sheet 141 used in the embodiment of FIG. 14A may be folded into two to sandwich the absorbent article 2 between the release region 141A and the protective region 141B. Also in this case, the packaging sheet 141 folded with its first surface directed inward can be sealed to itself outside the absorbent article 2 that is not folded.

In the foregoing first to fifth embodiments, the stack may be folded about a fold axis longitudinally crossing the absorbent article, i.e., a fold axis extending perpendicular to the fold axes transversely crossing the absorbent article.

In the foregoing first to sixth embodiments, a see-through sheet through which the outer shape of the absorbent article can be recognized is preferably used for the packaging sheet or the protective sheet covering the body surface of the absorbent article. If the absorbent article can be seen through the packaging sheet or the protective sheet, the direction and the position of the absorbent article can be confirmed visually when the pressure sensitive adhesive layer 7 on the garment surface of the absorbent article is adhered to the crotch portion of the undergarment while protecting the body surface of the absorbent article with the packaging sheet or the protective sheet. Therefore, accurate positioning of the absorbent article with respect to the crotch portion of the undergarment can be accomplished. In this case, the packaging sheet or the protective sheet may be formed by reducing a coloring agent such as pigment or dye to be contained in the sheet or without using such a coloring agent. Alternatively, the packaging sheet or the protective sheet may be formed of a sheet having a small basis weight or a thin sheet so that the absorbent article can easily be confirmed visually. Concrete examples include a coarse nonwoven fabric, an apertured film, an apertured nonwoven fabric, paper, a transparent film, and a translucent film containing a white pigment in an amount of 2% by weight or less.

In the foregoing first to sixth embodiments, the individual components may be formed of water-disintegratable materials. The water-disintegratable material as used herein means a material whose constituent fibers can be dispersed with a stream of wash water after disposed of in a flush toilet or a large amount of water of a septic tank.

FIG. 17A shows a hygiene product according to a seventh embodiment of the present invention, wherein the individual components are formed of water-disintegratable materials. In the hygiene product of FIG. 17A, both the structure and the packaged configuration by folding are identical to those of the first embodiment shown in FIGS. 1 to 5. However, the individual components are formed of materials different from those of the first embodiment.

An absorbent article 102 of the seventh embodiment is water-disintegratable.

A liquid permeable top layer 103 may comprise a stack of a plurality of water-disintegratable nonwoven fabrics and tissue paper disposed on one side of the stack to face the liquid absorbent layer, wherein the stack and the tissue paper are integrated and apertured to have liquid passage holes by embossing. The water-disintegratable nonwoven fabric may be prepared by forming a web from a blend of free pulp and rayon having a fineness of 1.1 dtex and a length of 7 mm in a wet-laid process and hydroentangling the web.

A back layer 104 may be water-disintegratable paper of which pulp is hydrogen bonded. In an alternative, the back layer 104 may be prepared by forming a web from water-dispersible fibers such as pulp or rayon and applying a water-soluble binder such as polyvinyl alcohol or copolymer of unsaturated carboxylic acid to bond the fibers. In another alternative, the back layer 104 may be prepared by hydroentangling a web of water-dispersible fibers and applying the water-soluble binder. Preferably, the back layer 104 is made impermeable to liquid by applying a water-proof resin such as cellulose ether or silicone to one surface of the back layer 104. In an alternative, cellulose ether and a polyester polyurethane resin that is biodegradable may be laminated to one surface of the back layer 104 so as to provide water proofing property.

For a liquid absorbent layer 105, a stack of a plurality of sheets of water-disintegratable paper, a sheet of air-laid pulp, a water-disintegratable nonwoven fabric, or a laminate of a sheet of air-laid pulp and polyvinyl alcohol may be used.

A pressure sensitive adhesive layer 107 provided on a garment surface of the back layer 104 may be formed by gravure coating an acrylic emulsion pressure sensitive adhesive. Such a pressure sensitive adhesive may comprise acrylic ester copolymer, styrene butadiene latex and a tackifier. If the absorbent article has wing portions as in the second embodiment, pressure sensitive adhesive layers to be provided on the wing portions can be formed in the same manner.

A release sheet 116 to be adhered to the pressure sensitive adhesive layer 107 may be a sheet which is prepared by applying a polyvinyl alcohol or copolymer of unsaturated carboxylic acid to one surface of a water-disintegratable nonwoven fabric or paper and laminating a release agent such as silicone to the surface coated with the copolymer.

A packaging sheet 115 may be a sheet similar to the back layer 104, such as a sheet prepared by applying polyvinyl alcohol or copolymer of unsaturated carboxylic acid to one surface of a water-disintegratable nonwoven fabric or paper.

Bonding between the top layer 103 and the back layer 104 and between the release sheet 116 and the packaging sheet 115 at a fixed portion 113 may be performed using a water-soluble or water-swellable hot-melt type adhesive. For such a hot-melt type adhesive, used can be made of a hot-melt containing: 58% copolymer comprising polyester polyol, polyoxyethylene polyoxypropylene glycol and polyvinyl acetate; and 27% terpene phenol as main component.

A fixed portion 118 where the water-disintegratable packaging sheet 115 and the water-disintegratable top layer 103 are detachably fixed to each other may be formed by using a water-soluble hot-melt adhesive. In an alternative, the fixed portion 118 may be formed as shown in FIG. 17B. In FIG. 17B, one surface of a substrate 118a that is water-disintegratable paper or the like is coated with an acrylic emulsion 118b similar to that used for the pressure sensitive adhesive layer 107 so as to be peelable from the top layer 103, and the other surface of the substrate 118a is adhered to the packaging sheet 115 through a water-soluble hot-melt type adhesive 118c similar to that used for the fixed portion 113.

In order to make the hygiene product disintegratable in water, it is preferred that the lead tape 12 is not used. Preferably, after folded, the packaging sheet 115 near an end edge 115a is adhered to a second surface 115b of the packaging sheet 115 through a water-soluble hot-melt. Side sealed portions similar to the side sealed portions 14 and 14 of FIG. 3B and the side sealed portions 14A and the sealed portion 18 of FIG. 15B may also be formed by adhering the packaging sheet 115 to itself through the water-soluble hot-melt type adhesive.

Also in the second embodiment, the third embodiment, the fourth embodiment, the fifth embodiment and the sixth embodiment, the individual components of the hygiene product can be formed of water-disintegratable materials as set forth above.

In the third embodiment, the fourth embodiment, the fifth embodiment and the sixth embodiment, it should also be noted that even if an engaging fastener having a large number of projections that can engage an inner side of an undergarment is provided on the garment surface 2B of the absorbent article 2 in place of the pressure sensitive adhesive layer 7, such an absorbent article can be wrapped in the packaging sheet.

According to the present invention, as has been described hereinabove, the top layer of the absorbent article can be prevented from contacting fingers or the like until the back layer of the absorbent article is adhered to a crotch portion of an undergarment. In addition, even when the pressure sensitive adhesive layer is pressed against the crotch portion of the undergarment, the top layer of the absorbent article can be prevented from directly contacting a hand.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. A hygiene product comprising:
   an absorbent article having a top layer for facing a wearer and a back layer having a pressure sensitive adhesive layer on a garment surface thereof; and
   a packaging sheet in which the absorbent article is wrapped, wherein the packaging sheet has a first surface and a second surface, at least 50% of the top layer of the absorbent article faces the first surface of the packaging sheet, and the pressure sensitive adhesive layer of the absorbent article is covered with a release sheet, wherein
   the absorbent article is wrapped in the packaging sheet such that the second surface of the packaging sheet appears externally, wherein
   the packaging sheet and the release sheet are connected to each other.

2. A hygiene product as set forth in claim 1, wherein the packaging sheet is detachably fixed to the top layer of the absorbent article through temporal attachment means.

3. A hygiene product as set forth in claim 1, wherein the absorbent article has a main body portion and a pair of wing portions extending outwardly from longitudinally extending side edges of the main body portion, wherein
   each wing portion has a second pressure sensitive adhesive layer on a garment surface thereof and is folded back against the release sheet so that the second pressure sensitive adhesive layer is adhered to the release sheet.

4. A hygiene product comprising:
   an absorbent article having a top layer for facing a wearer and a back layer on a side opposite the top layer; and
   a packaging sheet in which the absorbent article is wrapped, wherein
   the absorbent article is wrapped in the packaging sheet with the packaging sheet being detachably fixed to the top layer of the absorbent article through temporal attachment means.

5. A hygiene product comprising:
   an absorbent article having a top layer for facing a wearer and a back layer on a side opposite the top layer; and
   a packaging sheet in which the absorbent article is wrapped, wherein
   the absorbent article is wrapped in the packaging sheet with a protective sheet being detachably fixed to the top layer of the absorbent article through temporal attachment means.

6. A hygiene product comprising:
   an absorbent article having a top layer for facing a wearer and a back layer on a side opposite the top layer; and
   a packaging sheet in which the absorbent article is wrapped, wherein
   the packaging sheet has a first surface and a second surface, the packaging sheet is folded such that both the top layer and the back layer of the absorbent article are completely covered by the first surface of the packaging sheet, and the packaging sheet is detachably fixed to the top layer of the absorbent article through temporal attachment means, wherein
   the absorbent article is wrapped in the packaging sheet such that the second surface of the packaging sheet appears externally.

7. A hygiene product as set forth in claim 6, wherein the back layer has a pressure sensitive adhesive layer on a garment surface thereof and the first surface of the packaging sheet has a release-treated portion, wherein the pressure sensitive adhesive layer is adhered to the release-treated portion.

8. A hygiene product as set forth in claim 6, wherein individual side portions of the packaging sheet protruding transversely outwardly beyond transversely opposed side edges of the absorbent article are sealed.

9. A hygiene product comprising:
   an absorbent article having a top layer for facing a wearer and a back layer having a pressure sensitive adhesive layer on a garment surface thereof; and
   a packaging sheet in which the absorbent article is wrapped, wherein
   the packaging sheet has a first surface and a second surface, at least 50% of the top layer of the absorbent article faces the first surface of the packaging sheet, and the pressure sensitive adhesive layer of the absorbent article is covered with a release sheet, wherein
   the absorbent article is wrapped in the packaging sheet such that the second surface of the packaging sheet appears externally, wherein
   the absorbent article has a main body portion and a pair of wing portions extending outwardly from longitudinally extending side edges of the main body portion, wherein
   each wing portion has a second pressure sensitive adhesive layer on a garment surface thereof and is folded back against the release sheet so that the second pressure sensitive adhesive layer is adhered to the release sheet.

10. A hygiene product as set forth in claim 9, wherein the packaging sheet is detachably fixed to the top layer of the absorbent article through temporal attachment means.

11. A hygiene product as set forth in claim 9, wherein the packaging sheet and the release sheet are connected to each other.

12. A hygiene product comprising:
    an absorbent article having a top layer for facing a wearer and a back layer on a side opposite the top layer; and
    a packaging sheet in which the absorbent article is wrapped, wherein
    the packaging sheet has a first surface and a second surface, the packaging sheet is folded such that the first surface faces both the top layer and the back layer of the absorbent article, and the packaging sheet is detachably fixed to the top layer of the absorbent article through temporal attachment means, wherein
    the absorbent article is wrapped in the packaging sheet such that the second surface of the packaging sheet appears externally, wherein
    the back layer has a pressure sensitive adhesive layer on a garment surface thereof and the first surface of the packaging sheet has a release-treated portion, wherein the pressure sensitive adhesive layer is adhered to the release-treated portion.

13. A hygiene product as set forth in claim 12, wherein individual side portions of the packaging sheet protruding transversely outwardly beyond transversely opposed side edges of the absorbent article are sealed.

* * * * *